(12) United States Patent
Watanabe et al.

(10) Patent No.: US 12,054,698 B2
(45) Date of Patent: Aug. 6, 2024

(54) MULTILAYERED ORGAN-ON-A-CHIP SYSTEMS AND METHODS OF USE THEREOF

(71) Applicant: The Regents of the University of California, Oakland, CA (US)

(72) Inventors: Momoko Watanabe, Irvine, CA (US); Kenichiro Kamei, Kyoto (JP)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 17/670,404

(22) Filed: Feb. 11, 2022

(65) Prior Publication Data
US 2022/0259534 A1     Aug. 18, 2022

Related U.S. Application Data

(60) Provisional application No. 63/149,213, filed on Feb. 12, 2021.

(51) Int. Cl.
| | |
|---|---|
| *C12M 3/00* | (2006.01) |
| *C12M 1/00* | (2006.01) |
| *C12M 1/12* | (2006.01) |
| *C12M 1/42* | (2006.01) |
| *C12N 5/079* | (2010.01) |
| *G01N 33/50* | (2006.01) |

(52) U.S. Cl.
CPC ............ *C12M 21/08* (2013.01); *C12M 25/00* (2013.01); *C12M 29/04* (2013.01); *C12M 35/08* (2013.01); *C12N 5/0618* (2013.01); *G01N 33/5032* (2013.01); *G01N 33/5088* (2013.01); *C12N 2513/00* (2013.01)

(58) Field of Classification Search
None
See application file for complete search history.

(56) References Cited

U.S. PATENT DOCUMENTS 6,653,124 B1 * 11/2003 Freeman ............. F16K 99/0001
435/297.1

FOREIGN PATENT DOCUMENTS

WO    WO-2012166903 A1 * 12/2012 ........... A01N 1/0247

OTHER PUBLICATIONS

Deng et al. "A cell lines derived microfluidic liver model for investigation of hepatotoxicity induced by drug-drug interaction." Biomicrofluidics 13, 024101-1 to 024101-10 (2019). (Year: 2019).*
Pamies et al. "Biological and medical applications of a brain-on-a-chip." Experimental Biology and Medicine 2014; 239: 1096-1107. (Year: 2014).*
Wang et al. "Human brain organoid-on-a-chip to model prenatal nicotine exposure." Lab Chip, 2018, 18, 851-860. (Year: 2018).*
Abdalkader et al., "Multi-corneal barriers-on-a-chip to recapitulate eye blinking shear stress forces." Lab Chip 15 (2):4277-85 (2020).
Bagley et al., "Fused cerebral organoids model interactions between brain regions." Nat Methods 14(7):743-51 (2017).

(Continued)

*Primary Examiner* — William H. Beisner
(74) *Attorney, Agent, or Firm* — Gavrilovich, Dodd & Lindsey LLP

(57) ABSTRACT

The disclosure provides for multilayered organ-on-a-chip systems that can be used to generate topographic neural organoids, and uses thereof, including as models to study neurological disorders.

18 Claims, 16 Drawing Sheets

Specification includes a Sequence Listing.

(56) References Cited

OTHER PUBLICATIONS

Bain et al., Therapeutic development in the absence of predictive animal models of nervous system disorders: Proceedings of a workshop. National Academy of Sciences, Engineering, and Medicine. The National Academies Press. Washington, D.C. (2017).
Baudoin et al., "Tangentially migrating neurons assemble a primary cilium that promotes their reorientation to the cortical plate." Neuron 76(6):1108-22 (2012).
Bhaduri et al., "Cell stress in cortical organoids impairs molecular subtype specification." Nature 578(7793):142-148 (2020).
Birey et al., "Assembly of functional integrated human forebrain spheroids." Nature 545(7652):54-9 (2017).
Cea-Del Rio et al., "The contribution of inhibitory interneurons to circuit dysfunction in Fragile X Syndrome." Front Cell Neurosci 8:245 (2014).
Mukhopadhyay et al., "Differential effects of BMP signaling on parvalbumin and somatostatin interneuron differentiation." Development 136(15):2633-42 (2009).
Samarasinghe et al., "Identification of neural oscillations and epileptiform changes in human brain organoids." Nat Neurosci 24(10):1488-1500 (2021).
Watanabe et al., "Self-organized cerebral organoids with human specific features predict effective drugs to combat Zika virus infection." Cell Rep 21(2):517-32 (2017).
Watanabe et al., "TGF superfamily signaling regulates the state of human pluripotency and competency to create telencephalic organoids." Stem Cell Reports 17:2220-2238 (2022).

* cited by examiner

Top

Bottom

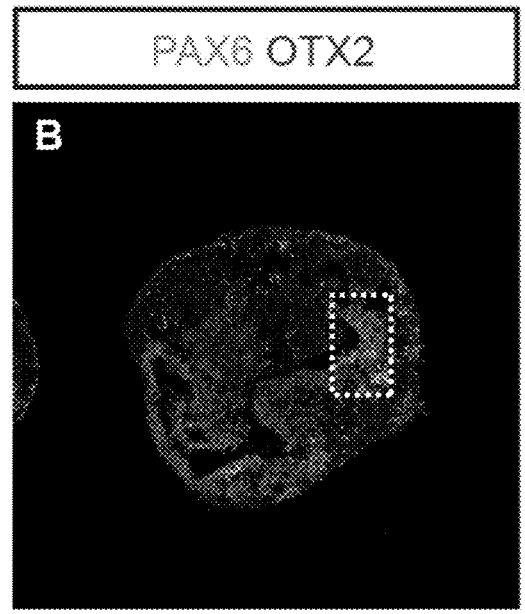
FIG. 9A  FIG. 9B
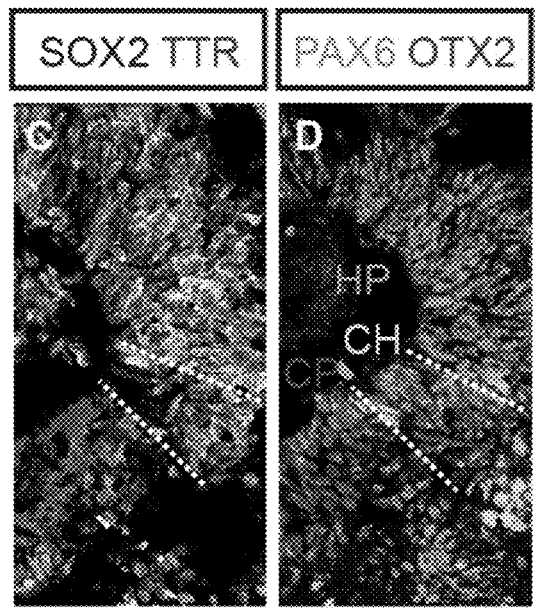
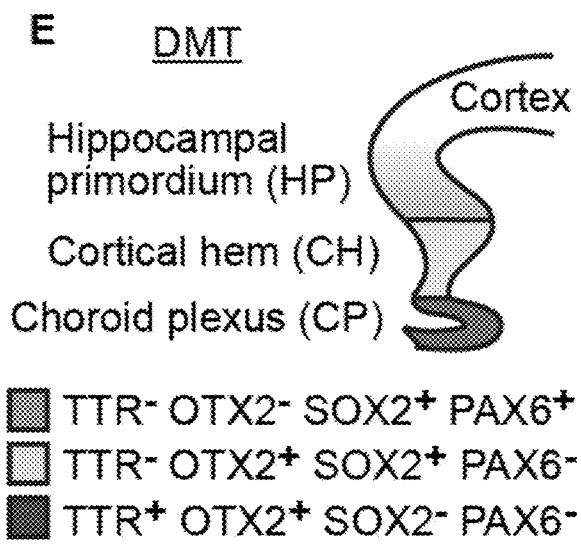
FIG. 9C  FIG. 9D  FIG. 9E

SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: B-Actin Fwd PCR Primer

<400> SEQUENCE: 1
agttctccag ctcgctcagc                                          20

<210> SEQ ID NO 2

```
<211> LENGTH: 22
<212> TYPE: DNA
<213> ORGANISM: Artificial Sequence
<220> FEATURE:
<223> OTHER INFORMATION: B-Actin Rev PCR primer

<400> SEQUENCE: 2
ggaaccatat cttcacctgc gt                                              22

<210> SEQ ID NO 3
<211> LENGTH: 21
<212> TYPE: DNA
<213> ORGANISM: Artificial Sequence
<220> FEATURE:
<223> OTHER INFORMATION: NANOG Fwd PCR primer

<400> SEQUENCE: 3
tttgtgggcc tgaagaaaac t                                               21

<210> SEQ ID NO 4
<211> LENGTH: 21
<212> TYPE: DNA
<213> ORGANISM: Artificial Sequence
<220> FEATURE:
<223> OTHER INFORMATION: NANOG Rev PCR primer

<400> SEQUENCE: 4
agggctgtcc tgaataagca g                                               21

<210> SEQ ID NO 5
<211> LENGTH: 19
<212> TYPE: DNA
<213> ORGANISM: Artificial Sequence
<220> FEATURE:
<223> OTHER INFORMATION: NKX2.1 Fwd PCR primer

<400> SEQUENCE: 5
agcacacgac tccgttctc                                                  19

<210> SEQ ID NO 6
<211> LENGTH: 22
<212> TYPE: DNA
<213> ORGANISM: Artificial Sequence
<220> FEATURE:
<223> OTHER INFORMATION: NKX2.1 Rev PCR primer

<400> SEQUENCE: 6
gcccactttc ttgtagcttt cc                                              22

<210> SEQ ID NO 7
<211> LENGTH: 19
<212> TYPE: DNA
<213> ORGANISM: Artificial Sequence
<220> FEATURE:
<223> OTHER INFORMATION: OCT4 Fwd PCR primer

<400> SEQUENCE: 7
ggagaagctg gagcaaaac                                                  19

<210> SEQ ID NO 8
<211> LENGTH: 20
<212> TYPE: DNA
<213> ORGANISM: Artificial Sequence
<220> FEATURE:
<223> OTHER INFORMATION: OCT4 Rev PCR primer

<400> SEQUENCE: 8
```
accttcccaa atagaacccc                                                    20

<210> SEQ ID NO 9
<211> LENGTH: 20
<212> TYPE: DNA
<213> ORGANISM: Artificial Sequence
<220> FEATURE:
<223> OTHER INFORMATION: OLIG2 Fwd PCR Primer

<400> SEQUENCE: 9
atagatcgac gcgacaccag                                                    20

<210> SEQ ID NO 10
<211> LENGTH: 20
<212> TYPE: DNA
<213> ORGANISM: Artificial Sequence
<220> FEATURE:
<223> OTHER INFORMATION: OLIG2 Rev PCR Primer

<400> SEQUENCE: 10
acccgaaaat ctggatgcga                                                    20

<210> SEQ ID NO 11
<211> LENGTH: 19
<212> TYPE: DNA
<213> ORGANISM: Artificial Sequence
<220> FEATURE:
<223> OTHER INFORMATION: OTX2 Fwd PCR Primer

<400> SEQUENCE: 11
agaggacgac gttcactcg                                                     19

<210> SEQ ID NO 12
<211> LENGTH: 21
<212> TYPE: DNA
<213> ORGANISM: Artificial Sequence
<220> FEATURE:
<223> OTHER INFORMATION: OTX2 Rev PCR Primer

<400> SEQUENCE: 12
tcgggcaagt tgattttcag t                                                  21

<210> SEQ ID NO 13
<211> LENGTH: 21
<212> TYPE: DNA
<213> ORGANISM: Artificial Sequence
<220> FEATURE:
<223> OTHER INFORMATION: PV Fwd PCR Primer

<400> SEQUENCE: 13
aagagtgcgg atgatgtgaa g                                                  21

<210> SEQ ID NO 14
<211> LENGTH: 22
<212> TYPE: DNA
<213> ORGANISM: Artificial Sequence
<220> FEATURE:
<223> OTHER INFORMATION: PV Rev PCR Primer

<400> SEQUENCE: 14
gccttttagg atgaatccca gc                                                 22

<210> SEQ ID NO 15
<211> LENGTH: 21
<212> TYPE: DNA

```
<213> ORGANISM: Artificial Sequence
<220> FEATURE:
<223> OTHER INFORMATION: SOX2 Fwd PCR Primer

<400> SEQUENCE: 15
gccgagtgga aactttttgtc g                                              21

<210> SEQ ID NO 16
<211> LENGTH: 22
<212> TYPE: DNA
<213> ORGANISM: Artificial Sequence
<220> FEATURE:
<223> OTHER INFORMATION: SOX2 Rev PCR Primer

<400> SEQUENCE: 16
ggcagcgtgt acttatcctt ct                                              22

<210> SEQ ID NO 17
<211> LENGTH: 21
<212> TYPE: DNA
<213> ORGANISM: Artificial Sequence
<220> FEATURE:
<223> OTHER INFORMATION: SST Fwd PCR Primer

<400> SEQUENCE: 17
acccaaccag acggagaatg a                                               21

<210> SEQ ID NO 18
<211> LENGTH: 20
<212> TYPE: DNA
<213> ORGANISM: Artificial Sequence
<220> FEATURE:
<223> OTHER INFORMATION: SST Rev PCR Primer

<400> SEQUENCE: 18
gccgggtttg agttagcaga                                                 20

<210> SEQ ID NO 19
<211> LENGTH: 21
<212> TYPE: DNA
<213> ORGANISM: Artificial Sequence
<220> FEATURE:
<223> OTHER INFORMATION: TFAP2C Fwd PCR Primer

<400> SEQUENCE: 19
ctgttgctgc acgatcagac a                                               21

<210> SEQ ID NO 20
<211> LENGTH: 21
<212> TYPE: DNA
<213> ORGANISM: Artificial Sequence
<220> FEATURE:
<223> OTHER INFORMATION: TFAP2C Rev PCR Primer

<400> SEQUENCE: 20
ctcagtgggg ttcattacgg c                                               21

<210> SEQ ID NO 21
<211> LENGTH: 22
<212> TYPE: DNA
<213> ORGANISM: Artificial Sequence
<220> FEATURE:
<223> OTHER INFORMATION: TFCP2L1 Fwd PCR Primer

<400> SEQUENCE: 21
ataccagccg tcctatgaaa cc                                              22
```

```
<210> SEQ ID NO 22
<211> LENGTH: 19
<212> TYPE: DNA
<213> ORGANISM: Artificial Sequence
<220> FEATURE:
<223> OTHER INFORMATION: TFCP2L1 Rev PCR Primer

<400> SEQUENCE: 22
actgcgagaa cctgttgcg                                              19

<210> SEQ ID NO 23
<211> LENGTH: 22
<212> TYPE: DNA
<213> ORGANISM: Artificial Sequence
<220> FEATURE:
<223> OTHER INFORMATION: TGFB1 Fwd PCR Primer

<400> SEQUENCE: 23
ctaatggtgg aaacccacaa cg                                          22

<210> SEQ ID NO 24
<211> LENGTH: 21
<212> TYPE: DNA
<213> ORGANISM: Artificial Sequence
<220> FEATURE:
<223> OTHER INFORMATION: TGFB1 Rev PCR Primer

<400> SEQUENCE: 24
tatcgccagg aattgttgct g                                           21

<210> SEQ ID NO 25
<211> LENGTH: 21
<212> TYPE: DNA
<213> ORGANISM: Artificial Sequence
<220> FEATURE:
<223> OTHER INFORMATION: TGFB3 Fwd PCR Primer

<400> SEQUENCE: 25
acttgcacca ccttggactt c                                           21

<210> SEQ ID NO 26
<211> LENGTH: 19
<212> TYPE: DNA
<213> ORGANISM: Artificial Sequence
<220> FEATURE:
<223> OTHER INFORMATION: TGFB3 Rev PCR Primer

<400> SEQUENCE: 26
ggtcatcacc gttggctca                                              19

<210> SEQ ID NO 27
<211> LENGTH: 21
<212> TYPE: DNA
<213> ORGANISM: Artificial Sequence
<220> FEATURE:
<223> OTHER INFORMATION: TTR Fwd PCR Primer

<400> SEQUENCE: 27
atccaagtgt cctctgatgg t                                           21

<210> SEQ ID NO 28
<211> LENGTH: 21
<212> TYPE: DNA
<213> ORGANISM: Artificial Sequence
<220> FEATURE:
```

<223> OTHER INFORMATION: TTR Rev PCR Primer

<400> SEQUENCE: 28
gccaagtgcc ttccagtaag a                                              21

<210> SEQ ID NO 29
<211> LENGTH: 21
<212> TYPE: DNA
<213> ORGANISM: Artificial Sequence
<220> FEATURE:
<223> OTHER INFORMATION: ZBTB20 Fwd PCR Primer

<400> SEQUENCE: 29
gacaggatct actcggcact c                                              21

<210> SEQ ID NO 30
<211> LENGTH: 20
<212> TYPE: DNA
<213> ORGANISM: Artificial Sequence
<220> FEATURE:
<223> OTHER INFORMATION: ZBTB20 Rev PCR Primer

<400> SEQUENCE: 30
actgcgccgc tgtaaaaaga                                                20

<210> SEQ ID NO 31
<211> LENGTH: 23
<212> TYPE: DNA
<213> ORGANISM: Artificial Sequence
<220> FEATURE:
<223> OTHER INFORMATION: ZEB1 Fwd PCR Primer

<400> SEQUENCE: 31
gatgatgaat gcgagtcaga tgc                                            23

<210> SEQ ID NO 32
<211> LENGTH: 21
<212> TYPE: DNA
<213> ORGANISM: Artificial Sequence
<220> FEATURE:
<223> OTHER INFORMATION: ZEB1 Rev PCR Primer

<400> SEQUENCE: 32
acagcagtgt cttgttgttg t                                              21

MULTILAYERED ORGAN-ON-A-CHIP SYSTEMS AND METHODS OF USE THEREOF

CROSS REFERENCE TO RELATED APPLICATIONS

This application claims priority under 35 U.S.C. § 119 from Provisional Application Ser. No. 63/149,213, filed Feb. 12, 2021 the disclosure of which is incorporated herein by reference.

TECHNICAL FIELD

The disclosure provides for multilayered organ-on-a-chip systems that can be used to generate topographic neural organoids, and uses thereof, including for studying neurological disorders and drug discovery.

SEQUENCE LISTING

The instant application contains a Sequence Listing which has been submitted electronically in ASCII format and is hereby incorporated by reference in its entirety. Said ASCII copy, created on Feb. 11, 2022, is named Sequence_ST25.txt and is 6,484 bytes in size.

BACKGROUND

The human brain has many features that are distinct to humans. To accurately understand mechanisms of human brain disease and identify novel therapies, direct access to human tissue is indispensable. However, ethical and practical concerns, including the limited availability of human brain samples at early fetal and postnatal stages, make it very difficult to conduct well-controlled experiments or test new therapies using human fetal/postnatal tissue. These considerations illustrate the need for alternative tools to study human brain cells with functional neural networks.

SUMMARY

The ability to generate topographic organoids containing diverse cell types is important for accurately understanding disease pathology because different cell types and brain regions are differentially affected in various diseases. To achieve precise topographic organization, the disclosure provides a "multilayered organ-on-a-chip" system to establish multi-concentration gradients in a 3D environment. The multilayered organ-on-a-chip system of the disclosure mimics developmental processes to create a properly formed telencephalon, including the GE, cortex with defined areal identities, DMT, and amygdala. The multilayered organ-on-a-chip systems disclosed herein can provide for the generation of brain organoids that have topographic organization of choroid plexus, hippocampal, cortical, antihem, lateral and media ganglionic eminence, and preoptic area (POA) regions. The multilayered organ-on-a-chip systems disclosed herein also can provide for the generation of cortical organoids with defined areal identities. The multilayered organ-on-a-chip systems disclosed herein also can provide for the generation of ganglionic eminence organoid. Additionally, the multilayered organ-on-a-chip systems disclosed herein can provide for the generation of organoids from the cells of subject's that have neurological disorders, thereby providing a platform for drug screening applications.

In a particular embodiment, the disclosure provides a A multilayered organ-on-a-chip system capable of generating three-dimensional molecular gradients, comprising: an organoid chamber configured to accommodate an organoid; a first porous membrane located on one side of the organoid chamber, wherein the first porous membrane allows for diffusion of a first fluid and an optional third fluid comprising cell factor(s), growth factor(s), cytokine(s) and/or differentiation factor(s) through the first porous membrane into the organoid chamber; a second porous membrane located on the opposite side of the organoid chamber from the first porous membrane, wherein the second porous membrane allows for diffusion of a second fluid and an optional fourth fluid comprising cell factor(s), growth factor(s), cytokine(s) and/or differentiation factor(s) through the second porous membrane into the organoid chamber; a first fluid inlet channel that is contact with the organoid chamber on one end and an inlet port on the other, wherein the first fluid channel is in fluid communication with the organoid chamber via the first porous membrane; a second fluid inlet channel that is in contact with the organoid chamber on one end and an inlet port on the other, wherein the second fluid inlet channel is in fluid communication with the organoid chamber via the second porous membrane; optionally, a third fluid inlet channel that is contact with organoid chamber on one end and an inlet port on the other, wherein the third fluid inlet channel is in fluid communication with the organoid chamber via the first porous membrane; optionally, a fourth fluid inlet channel that is in contact with the organoid chamber on one end and an inlet port on the other, wherein the fourth fluid inlet channel is in fluid communication with the organoid chamber via the second porous membrane; a first fluid outlet channel that is contact with organoid chamber, wherein the first fluid outlet channel is in fluid communication with the organoid chamber via the first porous membrane; a second fluid outlet channel that is contact with organoid chamber, wherein the second fluid outlet channel is in fluid communication with the organoid chamber via the second porous membrane; wherein the first fluid inlet channel, the second fluid inlet channel, the optional third fluid inlet channel, and the optional fourth fluid inlet channel are configured to flow fluids into the channels in a directional manner from the inlet ports to the organoid chamber; wherein the first fluid outlet channel is configured to flow fluids from the organoid channel to a first outlet port in a directional manner; wherein the second fluid outlet channel flow is configured to flow fluids from the organoid channel to a second outlet port in a directional manner; wherein introduction of the first, second, optional third and optional fourth fluids into the organoid chamber via the fluid inlet channels generates a molecular gradient by natural diffusion of factors found in the fluids into the organoid channel. In a further embodiment, the first porous membrane and the second porous membrane are comprised of a material selected from polyethylene terephthalate (PET), polycarbonate (PC), macro porous silicon, hydrophilic polytetrafluoroethylene (PTFE), polydimethylsiloxane (PDMS), cycloolefin polymer (COP), cyclo olefin co-polymer (COC), polystyrene (PS), polyvinyl chloride (PVC) polymethylmethacrylate (PMMA) and/or mixed cellulose esters. In another embodiment or a further embodiment herein, the organoid chamber comprises a primitive neuroepithelial organoid embedded in a hydrogel. In another embodiment or a further embodiment herein, the primitive neuroepithelial organoid is neurally differentiated from hPSCs, iPSCs, or ESCs. In another embodiment or a further embodiment herein, the hPSCs, iPSCs, or ESCs are generated from cells of a subject that has a genetic neurological disorder. In another embodiment or a further embodiment herein, the genetic neurological disorder is selected from the group consisting of Aicardi Syndrome, Alper's Disease, Batten Disease, Fabry Disease, Fahr's Syndrome, Gerstmann-Straussler-Scheinker Disease, Leigh's Disease, Lesch-Nyhan Syndrome, Menkes Disease, Moya Moya Disease, Niemann-Pick Disease, Zellweger Syndrome, Fragile X Syndrome, 2-hydroxygluraric aciduria, 3-hydroxy-3-methylglutaryl-CoA lyase deficiency, 3-methylcrotonyl-CoA carboxylase deficiency, adenylosuccinate lyase deficiency, alpha-mannosidosis, alpha-methylacyl-CoA racemase deficiency, aminoacylase 1 deficiency, arginase deficiency, argininosuccinic aciduria, aromatic L-amino acid decarboxylase deficiency, aspartylglucosaminuria, beta-ketothiolase deficiency, beta-mannosidosis, biotinidase deficiency, childhood myocerebrohepatopathy spectrum, citrullinemia, Coats plus syndrome, combined malonic and methylmalonic aciduria, dentatorubral-pallidoluysian atrophy, deoxyguanosine kinase deficiency, dihydrolipoamide dehydrogenase deficiency, dihydropyrimidine dehydrogenase deficiency, ethylmalonic encephalopathy, fucosidosis, fumarase deficiency, GABA-transaminase deficiency, galactosemia, GLUT1 deficiency syndrome, glutamate formiminotransferase deficiency, glutaric acidemia type I, glutathione synthetase deficiency, GM1 gangliosidosis, GRIN2B-related neurodevelopmental disorder, guanidinoacetate methyltransferase deficiency, hypermethioninemia, hyperprolinemia, isovaleric acidemia, L1 syndrome, Leigh syndrome, malonyl-CoA decarboxylase deficiency, MECP2-related severe neonatal encephalopathy, MEGDEL syndrome, mitochondrial complex III deficiency, mitochondrial neurogastrointestinal encephalopathy disease, molybdenum cofactor deficiency, mucolipidosis type IV, mucopolysaccharidosis type I, mucopolysaccharidosis type II, mucopolysaccharidosis type III, multiple sulfatase deficiency, myoclonic epilepsy with ragged-red fibers, N-acetylglutamate synthase deficiency, nonketotic hyperglycinemia, ornithine transcarbamylase deficiency, phosphoglycerate dehydrogenase deficiency, phosphoglycerate kinase deficiency, phosphoribosylpyrophosphate synthetase superactivity, PMM2-congenital disorder of glycosylation, prion disease, prolidase deficiency, pyruvate dehydrogenase deficiency, Schindler disease, short/branched chain acyl-CoA dehydrogenase deficiency, sialic acid storage disease, succinic semialdehyde dehydrogenase deficiency, and X-linked creatine deficiency. In another embodiment or a further embodiment herein, the genetic neural disorder is Fragile X Syndrome. In another embodiment or a further embodiment herein, the first fluid comprises different types and/or different concentrations of cell, growth, cytokine and/or differentiation factors than the second fluid. In another embodiment or a further embodiment herein, the first fluid comprises high concentrations of dorsalizing/caudalizing factors. In another embodiment or a further embodiment herein, the dorsalizing/caudalizing factors is BMP4 and WNT3A. In another embodiment or a further embodiment herein, the second fluid comprises high concentrations of a ventralizing or rostralizing factor. In another embodiment or a further embodiment herein, the ventralizing or rostralizing factor is SHH or FGF8. In another embodiment or a further embodiment herein, the introduction of the fluids generates a multi-concentration gradient that promotes the further differentiation of the primitive neuroepithelial organoid into a topographic neural organoid. In another embodiment or a further embodiment herein, the topographic neural organoid is a brain organoid, a cortical organoid, or a ganglionic eminence organoid. In another embodiment or a further embodiment herein, the brain organoid has topographic organization of the choroid plexus, hippocampal, cortical, antihem, and/or lateral and media ganglionic eminence regions. In another embodiment or a further embodiment herein, the brain organoid is a brain organoid derived from cells of a subject that has a genetic neurological disorder. In another embodiment or a further embodiment herein, the brain organoid is a Fragile X Syndrome brain organoid.

In another embodiment, the disclosure also provides methods for screening drugs or agents for their effects on a brain organoid derived from cells of a subject that has a genetic neurological disorder using a multilayered organ-on-a-chip system of the disclosure, comprising: contacting the brain organoid with one or more drugs or agents; assessing the effects of the one or more drugs or agents on the brain organoid activity and/or function. In a further embodiment, the brain organoid is contacted with the one or more drugs or agents by introducing one or more drugs or agents into the one or more of the fluid inlet channels. In yet a further embodiment, the network activities in the cortical region of the brain organoid are assessed.

In a particular embodiment, the disclosure also provides a brain organoid, a cortical organoid, or a ganglionic eminence organoid produced using a multilayered organ-on-a-chip system of the disclosure. In a further embodiment, the brain organoid is a Fragile X Syndrome brain organoid.

DESCRIPTION OF DRAWINGS

FIG. 9A-E provides the topographic organization of the dorsal telencephalon. Telencephalic organoids were exposed to dorsal morphogen gradients (BMP4, 5 ng/mL). The dorsomidline telencephalone (DMT), including the choroid plexus (CP), cortical hem (CH), and hippocampal primordium (HP), was formed adjacent to the cortical area (A-D). The identity of each region was demonstrated by a combination of markers, noted in (E).

DETAILED DESCRIPTION

Figure 1A:
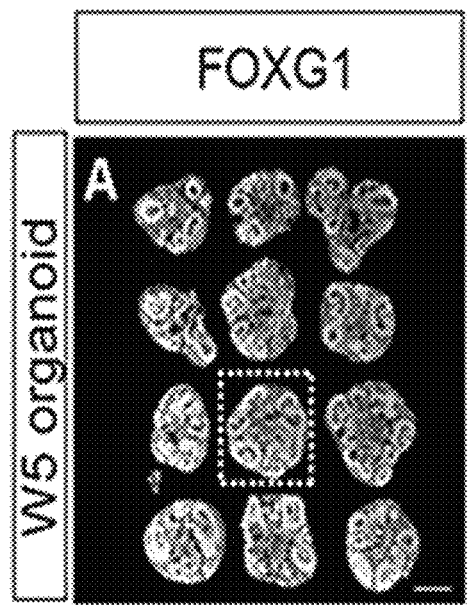
FIG. 1A-G presents photos of human neocortical organoids derived from hPSCs. (A-E) Highly efficient cortical induction showing expression of canonical forebrain markers. (F-G) Comparative immunohistochemical analyses of in vitro, week 8 cerebral organoids and gestational week 14 human fetal cortex.
Figure 1B:
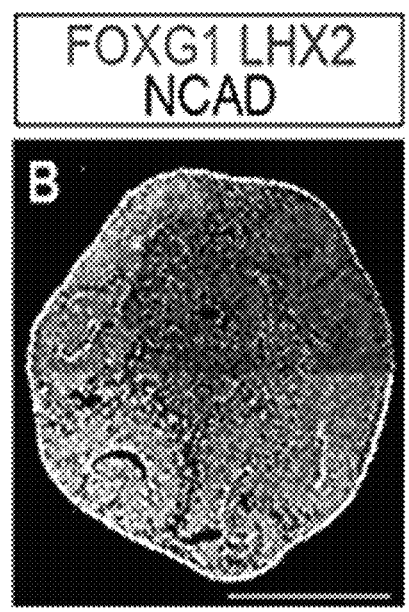
Figure 1C:
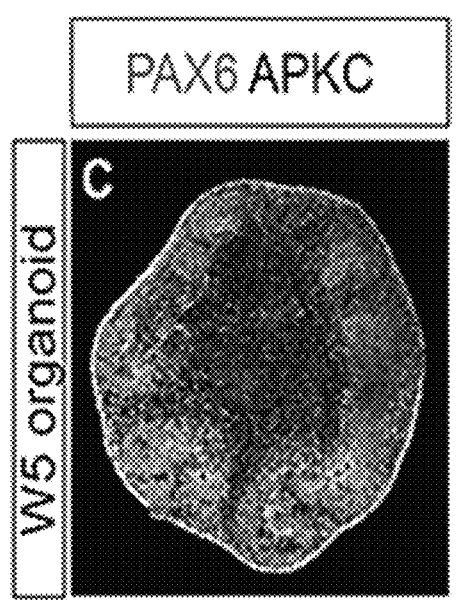
Figure 1D:
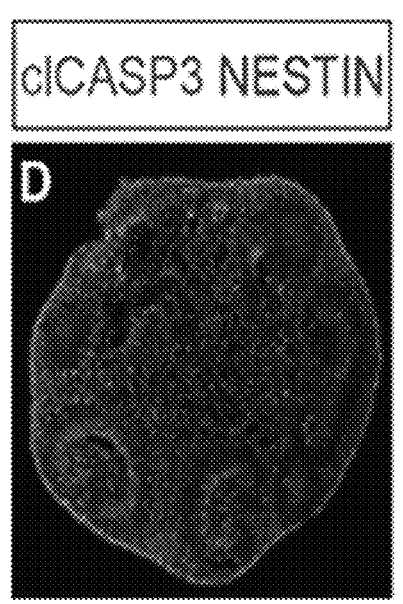
Figure 1E:
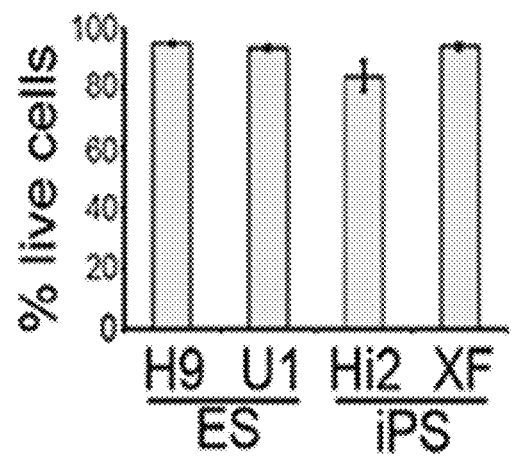
Figure 1F:
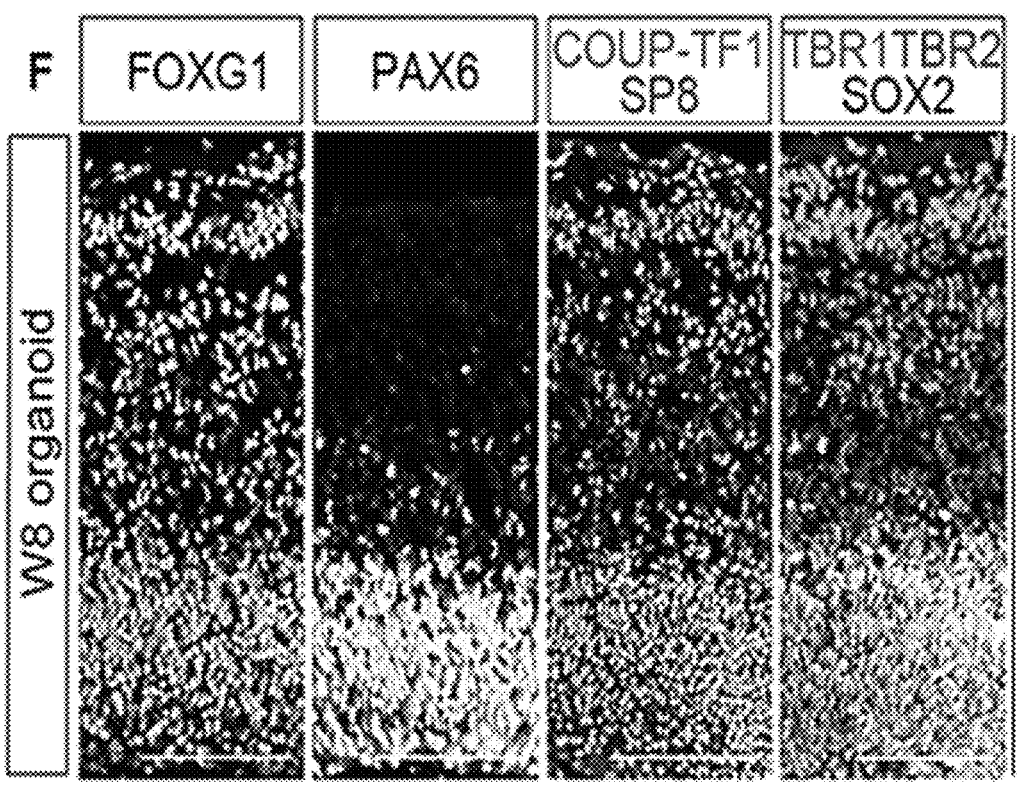
Figure 1G:
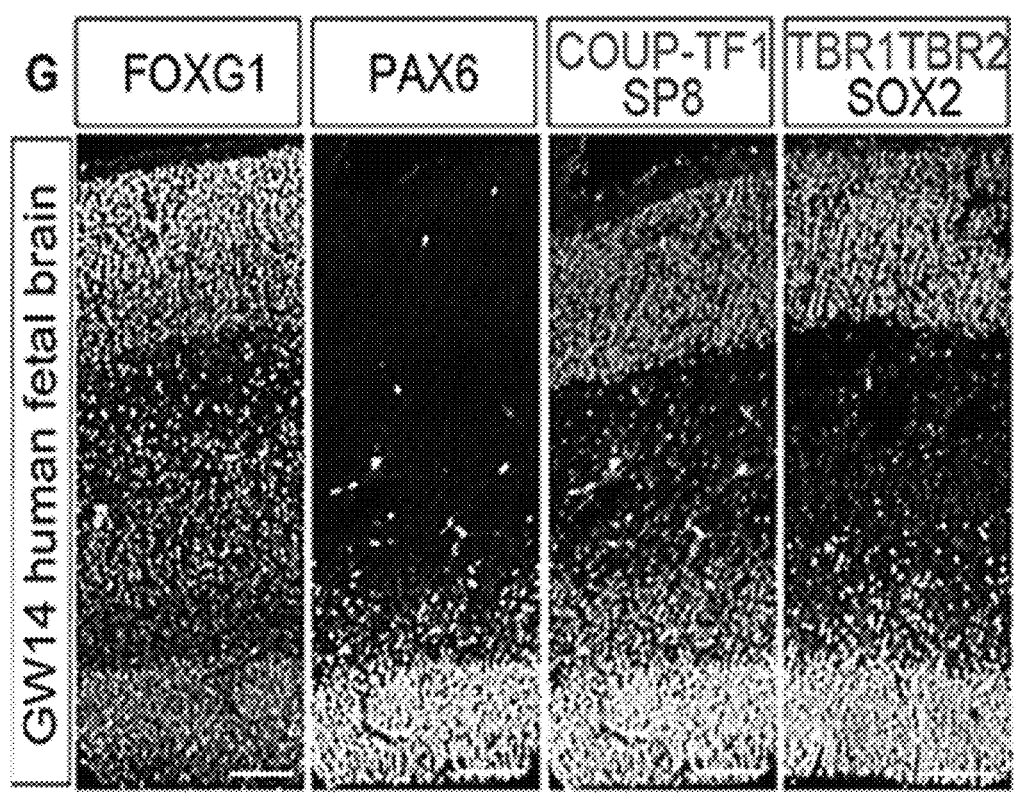
Figure 2A:
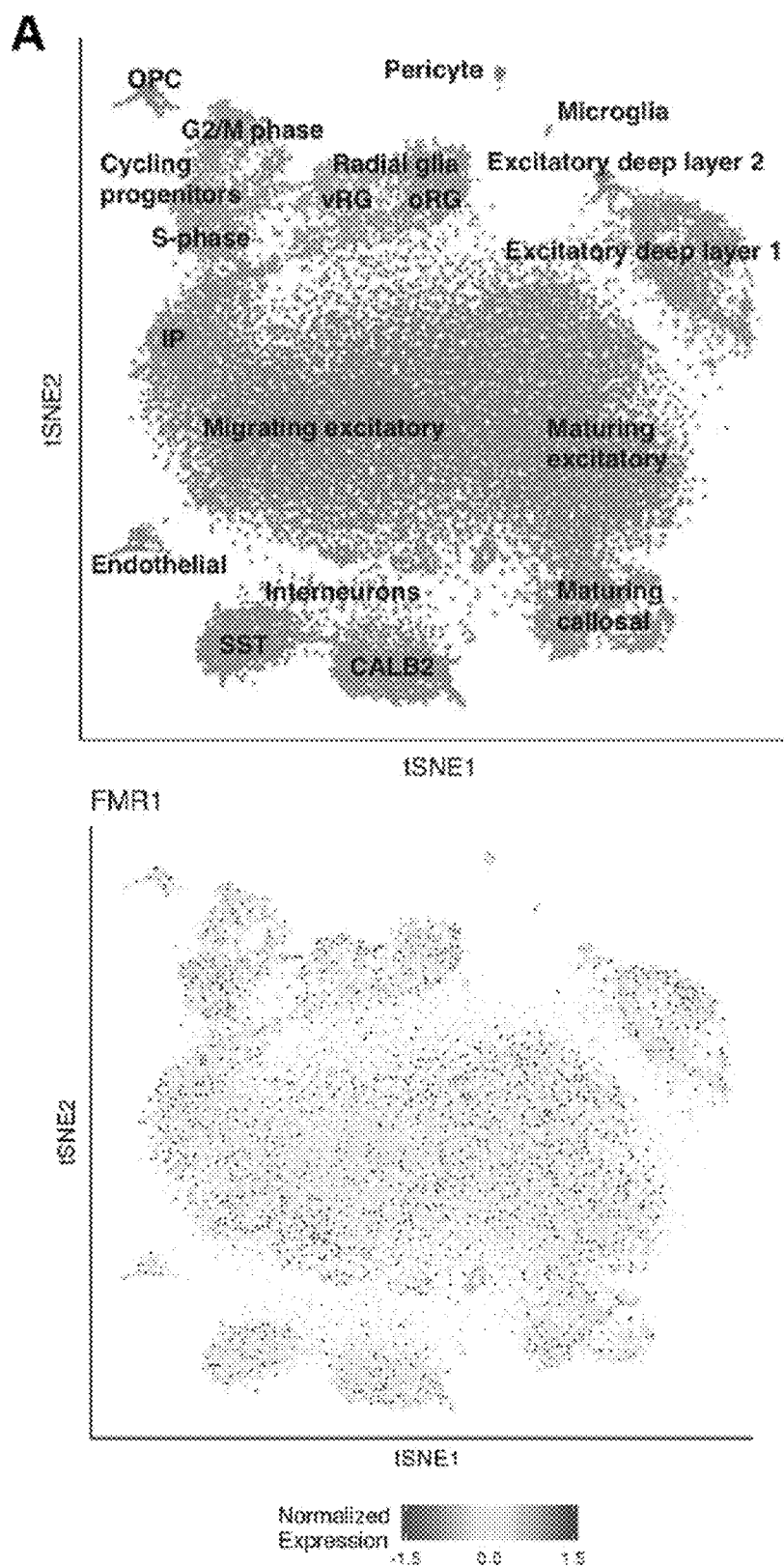
FIG. 2A-E presents the expression levels in human fetal cortex and cortical organoids. (A-B) FMR1 expression in midgestational human cortex by single-cell RNA sequencing in many cell types including progenitors, excitatory, and inhibitory neurons. (C-E) FMR1 expression in a cortical organoid at 10 weeks old by immunostaining. FMR1 expression is well observed in PAX6 positive progenitors and CTIP2 positive neurons consistent with the single-cell RNA sequencing data.
Figure 2B:
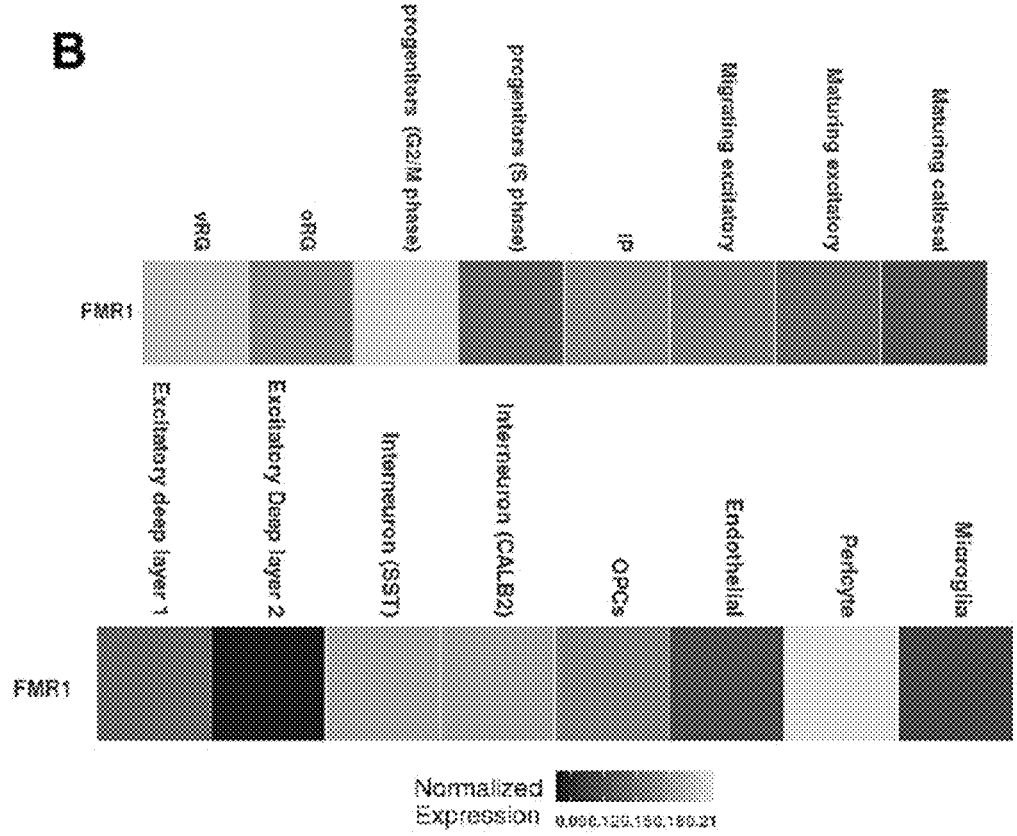
Figure 2C:
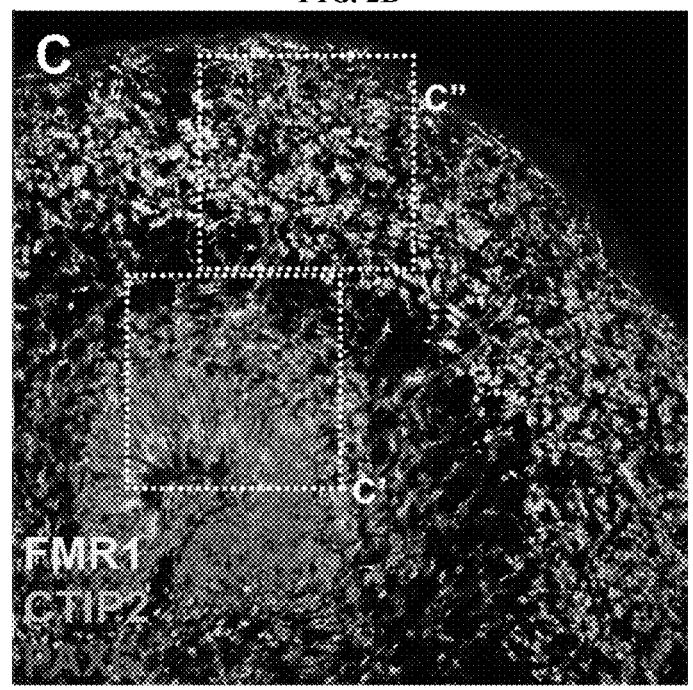
Figure 2D:
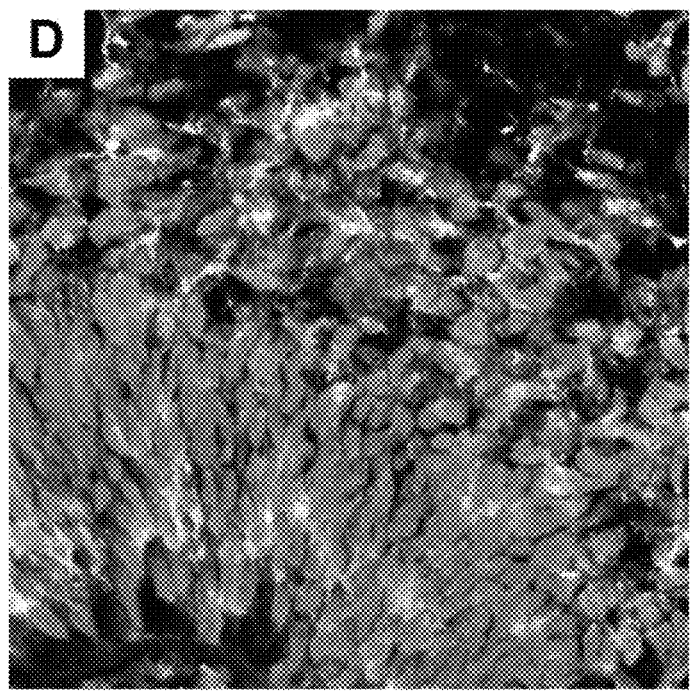
Figure 2E:
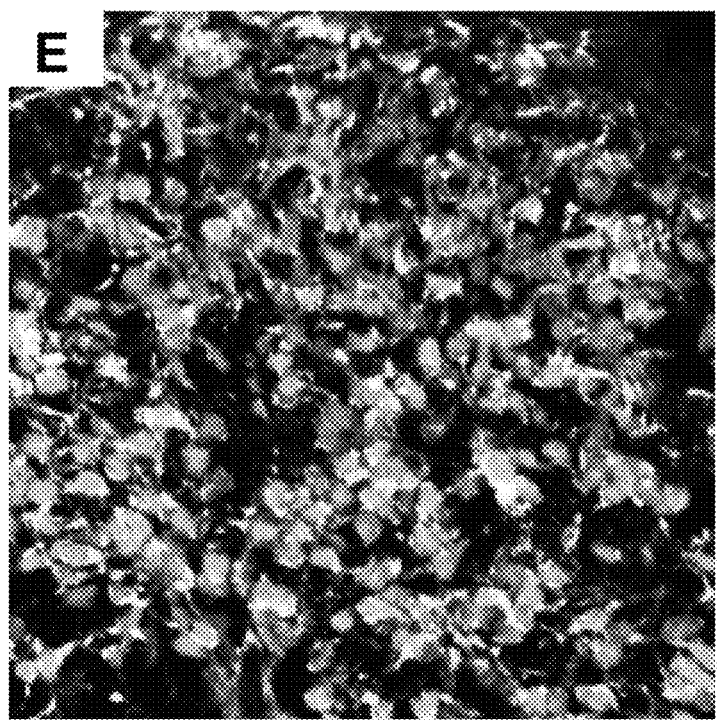

As used herein and in the appended claims, the singular forms "a", "an", and "the" include plural referents unless the context clearly dictates otherwise. Thus, for example, reference to "a neurosphere" includes a plurality of such neurospheres and reference to "the organoid" includes reference to one or more organoids and equivalents thereof known to those skilled in the art, and so forth.

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated by reference in full for the purpose of describing and disclosing methodologies that might be used in connection with the description herein. The publications are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

As used herein, the term "differentiation" refers to the process where a cell changes from one cell type to another, e.g., a neural progenitor cell (NPC) differentiates into a neuron or glial cell. Differentiation dramatically changes a cell's size, shape, membrane potential, metabolic activity, and responsiveness to signals. These changes are largely due to highly controlled modifications in gene expression.

As used herein, the term "organoids" refers in vitro grown three-dimensional structures that recapitulate key aspects of human development and disease which have been induced from human pluripotent stem cells (hPSCs). The conditions and gradients used with the multilayered organ-on-a-chip systems can give rise to different types of organoids, including, but not limited to, brain organoids, cortical organoids, and amygdala organoids.

As used herein, the term "high throughput screening" refers to a method for scientific experimentation especially used in drug discovery that can rapidly identify active compounds, small molecules, polypeptides, antibodies, biologically active oligonucleotides or genes that modulate a particular biomolecular pathway. High-throughput screening allows a researcher to quickly conduct thousands if not millions of chemical, genetic, or pharmacological tests. Typically, "high throughput screening" is automated by use of robotics, data processing/control software, liquid handling devices, and sensitive detectors.

As used herein, the term "neurodegenerative insult" refers to an action, such as by exposure to a chemical, microorganism, substance, or injury, etc., that leads to neurodegeneration. Examples of "neurodegenerative insults" include, but are not limited to, reperfusion injuries, protein aggregation (e.g., Alzheimer's or Parkinson associated proteins), reactions of free radicals, insufficient blood supply, glutamate excitotoxicity, and oxidative stress. Other neurodegenerative insults are known in the art.

As used herein the term "neurological disease", "neurological disorder" or "neurological condition" refers to a disease of the brain, spine and nerves that connect them. There are more than 600 diseases of the nervous system, such as brain tumors, epilepsy, Parkinson's disease and stroke. Major types of neurological diseases, disorders or conditions include, but are not limited to, diseases caused by faulty genes (e.g., Fragile X Syndrome, Huntington's disease and muscular dystrophy); problems with the way the nervous system develops (e.g., spina *bifida*); degenerative disease where nerve cells are damaged or die (e.g., Parkinson's disease or Alzheimer's disease); diseases of the blood vessels that supply the brain (e.g., stroke); injuries to the spinal cord or brain; seizure disorders (e.g., epilepsy); cancer (e.g., brain tumors); and infections (e.g., meningitis).

As used herein, the term "neuroprotective effect" refers to a compound or agent that has the effect of preserving neuronal structure and/or function. In the case of a neurodegenerative insult, the compound or agent provides for the relative preservation of neuronal integrity, such that the rate of loss of neural integrity is reduced in the presence of the compound or agent than without.

As used herein, the term "neural progenitor cells" or "NPCs" refers to cells capable of dividing a limited number of times and have the capacity to differentiate into a restricted repertoire of neuronal and glial cell types.

As used herein, the term "neurobasal media" refers to cell or organoid growing basal medium that is designed for long-term maintenance and maturation of substantially pure or pure pre-natal and embryonic neuronal cell populations without the need for an astrocyte feeder layer when supplemented. Neurobasal media is commercially available from a variety of vendors, including ThermoFisher™ Scientific, VWR™, Sigma Aldrich™, US Bio™, and STEMCELL™ Technologies.

As used herein, the term "stem cells" refers to an undifferentiated cell of a multicellular organism that is capable of giving rise to indefinitely more cells of the same type, and from which certain other kinds of cell arise by differentiation.

As used herein, the term "supplemented neurobasal media" refers to neurobasal media that has been supplemented with factors and growth agents that promote the survival, growth and differentiation of neuronal cells.

Supplements for neurobasal media can be purchased from a variety of vendors, including B-27™ Plus, N-2 and GlutaMAX™ supplements from ThermoFisher Scientific, NeuroCult™ and STMdiff™ supplements from STEMCELL Technologies, GEM21 NeuroPlex™ and N2 NeuroPlex™ from Gemini Bio-Products, and NDiff™ supplements from Sigma Aldrich.

As used herein, the term "vehicle control" refers to substance that is used as a vehicle for a solution of the experimental compound or drug product, which is used alone and is administered in the same manner as it is used with the experimental compound or drug product. Typically, the "vehicle control" is innocuous and does not change the activity of the cells or organoids disclosed herein.

The human brain has many features that are distinct to humans. To effectively understand human disease mechanisms and identify novel therapies, it is important to have access to a human tissue-based model for experimental study. However, ethical and practical concerns, including the limited availability of human brain samples at early fetal and postnatal stages, make it very difficult to conduct well-controlled experiments and drug screening with fetal and postnatal tissue. These considerations illustrate the need for alternative tools to study human brain cells with functional neural networks. In vitro models, termed human brain organoids (aka "mini-brains in a dish) are three-dimensional (3D) tissue structures induced from human pluripotent stem cells (hPSCs). Organoid technology has enormous potential as a tool for discovering new human-specific treatments where animal models for many neurological disorders have consistently failed. Currently, region-specific forebrain organoids are restricted to a single domain because they are induced by bath application of signaling molecules. To mimic dorsoventral tissue interactions in vivo, many groups fuse cortical and ganglionic eminence like organoids. However, this approach does not provide some key signaling molecules from spatial organizers that create morphogen gradients, which are important for cell specification and diversification and circuit maturation. While the assembly approach is a good system to study some aspects of tissue interactions and interneuronopathies, it is limited since it introduces technical variability when docking and batch-to-batch variability in interneuronal migration has been observed.

Provided herein is an organoid platform capable of growing the entire dorsoventral or rostrocaudal telencephalon together, without need for assembly by establishing morphogen gradients. In particular, disclosure provides for a "multilayered organ-on-a-chip" system to establish multi-concentration gradients in a 3D environment to achieve precise topographic organization of the resulting organoids. The multilayered organ-on-a-chip system of the disclosure mimics developmental processes to create a properly formed telencephalon, including the POA, GE, cortex with defined areal identities, DMT, and amygdala. Further provided herein are organoids that closely mimic the developmental transition of human fetal cortex transcriptionally, architecturally, and functionally. By accurately creating the entire telencephalon in vitro, human neural development can be systematically evaluated from tracking events that are likely occurring in the embryo to evaluate functional circuit maturation in unprecedented details.

The enhanced topographic organoid technology disclosed herein allows for the discovery of new insights into neurological disorders, such as Fragile X Syndrome (FXS). FXS is the most common inheritable form of intellectual disability and a monogenetic cause of autism spectrum disorder. Specific brain regions, such as the cortex, hippocampus, basal ganglia, and amygdala, are markedly affected in FXS. Thus, the ability to generate consistent topographic organoids containing different brain regions and diverse cell types is important for accurately understanding disease pathology. Accordingly, the disclosure provides for the modeling of the developing human telencephalon, which heretofore was not available, which can be used to investigate human-specific features of brain development, function, and disease. The methods, systems and compositions of the disclosure are readily tunable and can be modified to study of development and testing of therapies for a wide variety of neurological diseases.

It is important to make highly efficient and uniform primitive neuroepithelial organoids that respond to extrinsic cues to become different regions of the brain. If unwanted cell types are formed, they could secrete factors that bias the cell specification of the neuroepithelial cells to an undesired fate. Thus, highly naïve and uniform neuroepithelial cells are important since their behavior when exposed to morphogen gradients in the multilayered organoid-on-a-chip systems is predictable. Using the methods described herein, highly efficient and robust neuroepithelial organoid differentiation can be realized.

The disclosure demonstrates the formation of small-scale functional electrophysiological networks in cortical organoids, similar to those observed in the developing brain. The generation of cerebral organoids from human pluripotent stem cells (hPSCs), human embryonic stem cells (hESCs) or induced pluripotent stem cells (iPSCs) offers a three-dimensional framework to study the developing human brain. Organoids generated from hPSCs, hESCS, or IPSCs provide a scaled-down and three-dimensional model of the human brain, mimicking various developmental features at the cellular and molecular level. Needless to say, the ability to model the complex functional dynamics of the human brain for research and therapeutic purposes is paramount. The organoids do not suffer from any the limitations seen with in vivo models, and can additionally be used in high-throughput studies which are clearly not possible in vivo.

Pluripotent stem cells are a type of cell that undergo self-renewal while maintaining an ability to give rise to all three-germ layer-derived tissues and germ cell lineages. Induced pluripotent stem cells are described by Shinya Yamanaka's team at Kyoto University, Japan. Yamanaka had identified genes that are particularly active in embryonic stem cells and used retroviruses to transfect mouse fibroblasts with a selection of those genes. Eventually, four key pluripotency genes essential for the production of pluripotent stem cells were isolated; Oct-3/4, Sox2, c-Myc, and Klf4. The same group published a study along with two other independent research groups from Harvard, MIT, and the University of California, Los Angeles, showing successful reprogramming of mouse fibroblasts into iPS and even producing a viable chimera. The methods of obtaining iPS cells are known and described in the literature (see, U.S. Pat. No. 9,005,966 and U.S. Pat. Publ. No. 2015/0159143A1, the disclosure of which are incorporated herein by reference). Briefly, terminally differentiated human fibroblast (e.g., human dermal fibroblasts) cells can be induced to de-differentiate. The disclosure contemplates the use of a variety of de-differentiation agents comprising KLF4, OCT4, SOX2, c-MYC or n-MYC, NANOG or any combination thereof (e.g., KLF4, OCT4, SOX2, c-MYC or n-MYC and optionally NANOG). Such de-differentiation agents include nucleic acids, peptides, polypeptides, small organic molecules, and antibodies that cause induction of any one or more of KLF4, OCT4, SOX2, c-MYC or n-MYC and NANOG. De-differentiation may be achieved by contacting a cell in vitro with one or more de-differentiation factors for a time sufficient to induce de-differentiation. In one aspect, the de-differentiation factors are transfected into a cell to be de-differentiated under the control of a constitutive or inducible promoter, or as RNA replicons comprising multicistronic RNA molecule separated by cleavable peptides (e.g., 2A peptides and/or IRES domains).

Cell types that can be used in the methods and organoids of the disclosure include stem cells derived from any mammalian species including humans, monkeys, and apes and include embryonic stem cells, embryonic germ cells, and iPS cells (see, e.g., Nature, 448:313-318, July 2007; and Takahashi et al., Cell, 131(5):861-872; which are incorporated herein by reference). Stem cells can be induced to differentiate down a desired lineage using a number of techniques known in the art including, but not limited to, physical stimuli, chemical/biological factor stimuli (e.g., growth factors, media conditions), co-culturing techniques and any combination of the foregoing.

Methods for making organoids include a number of steps including (i) inducing neural progenitor cells development from stem cells, (ii) expanding/proliferating the neuronal progenitor cells, (iii) inducing neural cell differentiation and (iv) stimulating neural cell maturation. For example, methods to produce organoids from human pluripotent stem cells (hPSCs) is described in the Examples section herein. Additional methods known in the art may also be used.

Additional sources of cells useful in the disclosure are include embryonic stem cells and induced pluripotent stem cells (iPSCs). Of particular advantage is that hPSCs, ESCs, and iPSCs can be obtained from subjects with various neurological diseases and disorders caused by genetic abnormalities. Thus, hPSCs, ESCs, and iPSCs obtained from the cells of these subjects will contain the genetic abnormality. Moreover, organoids derived from these cells will include the abnormality. Such "abnormal" organoids can then be used to study the disease and screen for treatments. Additionally, hPSCs, ESCs, and iPSCs from a normal patient can be gene edited to provide for "abnormal" organoids that can also be used to study and screen for treatments for neurological diseases, disorders or conditions. Examples of techniques for gene editing include, but are not limited to, viral systems, meganuclease-based engineering, zinc finger nuclease-based engineering, TALEN, and CRISPR-Cas systems or the like.

The somatic cells used to obtain iPSCs cells can be isolated from any number of various tissues of the body. For example, cells may be obtained from bone marrow, fetal tissue (e.g., fetal liver tissue), peripheral blood, umbilical cord blood, pancreas, skin and the like. In one embodiment, the cells are fibroblasts and in a further embodiment, the cells are obtained from a subject having, or suspected of having, a mutation that causes a neurological disease or disorder. As is known in the art, a somatic cell includes the genetic makeup of the individual and thus any induced pluripotent stem cell obtained from the somatic cell will include the same genetic makeup (e.g., same mutations found in the somatic cells obtained from the subject).

The methods of the disclosure may be applied to a procedure wherein differentiated (lineage committed) cells are harvested from a subject, de-differentiated in culture, manipulated to re-differentiate along a specific differentiation pathway (e.g., neuronal cells) and then cultured and studied to (a) determine a mutations phenotypic result and/or (b) screen agents for their effect on the mutant dedifferentiated neuronal cell. Moreover, a portion of the cells removed from the subject can be gene edited, e.g., introduce mutations in gene(s), while another portion may be left, as harvested, thereby providing for both 'control' and 'abnormal' cells for further experiments.

For example, fibroblasts can be removed from a subject, de-differentiated using de-differentiation factors (e.g., with a KLF4, OCT4, SOX2, c-MYC or n-MYC, NANOG agonists or any combination thereof) and optionally mitotically expanded and then differentiated with factors (including physical stimuli) known to cause differentiation of iPSCs down a lineage committed path. In one embodiment, the method comprises removing differentiated cells from an injured or diseased subject. In one embodiment, the "de-differentiated cells" are differentiated down a lineage committed path to study a particular disease. For example, the de-differentiated cells (e.g., iPSC) can be differentiated down a neuronal lineage to obtain organoids.

The isolation of cells, such as fibroblasts, from a subject are known. For example, the isolation of fibroblasts may, for example, be carried out as follows: fresh tissue, e.g., a biopsy, samples are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. Fibroblasts cells will attach to the culture dish before other cells; therefore, appropriate stromal cells can be selectively isolated and grown.

Somatic cells (e.g., a population of somatic cells such as fibroblasts) are obtained from a subject are de-differentiated into induced pluripotent stem cells (iPSCs). For mutations having effects on neuronal processing and development, the iPSCs are then differentiated to neuronal cells (e.g., such as into organoids). Because the genome of the iPSCs will carry any mutant gene present in the somatic cell, the differentiated neuronal cells will also carry the same mutation. In this way, the effect of the mutation on neuronal function can be studied. In addition, various factors or agents can be used to modulate the effect of the mutation on neuronal cell function, which may further be specific for the subject that was the source of the cells. In other words, the differentiated neuronal cells can be used to screen agents for effects on the biological function of the mutant neuronal cells. In this way, agents that show a beneficial effect on a particular mutation can then be advanced as potential therapeutics.

iPSCs can be cultured and expanded using number of known methods. In some embodiments, the stem cells are cultured using a feeder system. In other embodiments the stem cells are cultured in a feeder free system. In yet another embodiment, the stem cells are cultured in a feeder free animal free culture system (see, U.S. Pat. No. 8,609,417, which is incorporated herein by reference). The cultured stem cells (e.g., hPSCs) can be stored (i.e., "banked") using commonly known techniques.

Microfluidic systems offer intrinsic advantages over conventional macroscopic cell culture such as reduced sample/reagent consumption and precise control over the delivery of culture fluids and soluble factors (e.g., growth factors and cytokines). The multilayered organ-on-a-chip system of disclosure is a microfluidic system that provides precise and consistent molecular gradients to organoids, thereby promoting consistent and reproducible topographic brain organoids. Thus, the multilayered organ-on-a-chip system of disclosure is superior to other technologies that rely on focally activating ventral patterning signals by doxycycline, leading to variability in the size of each domain from organoid-to-organoid.

Figure 3A:
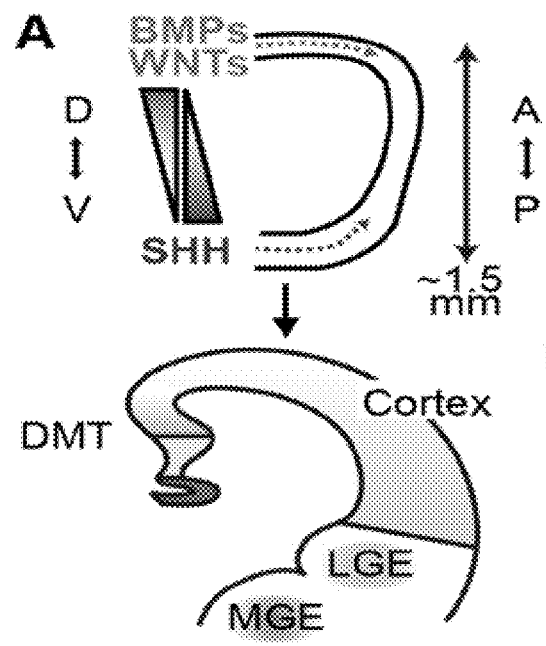
FIG. 3A-D provides a schematic representation of the telencephalon and microfluidic gradient device. (A) The early telencephalon showing the morphogen gradients and topographic regions: dorsomedial telencephalon (DMT), cortex, and ganglionic eminence (GE), and defined areal identities in the cortex. (B) Organoids will be embedded in a hydrogel and placed in the chamber to establish the dorsoventral axis of the telencephalon to form different domains. (C, D) Pictures of an exemplary multilayered organ-on-a-chip system of the disclosure.
Figure 3B:
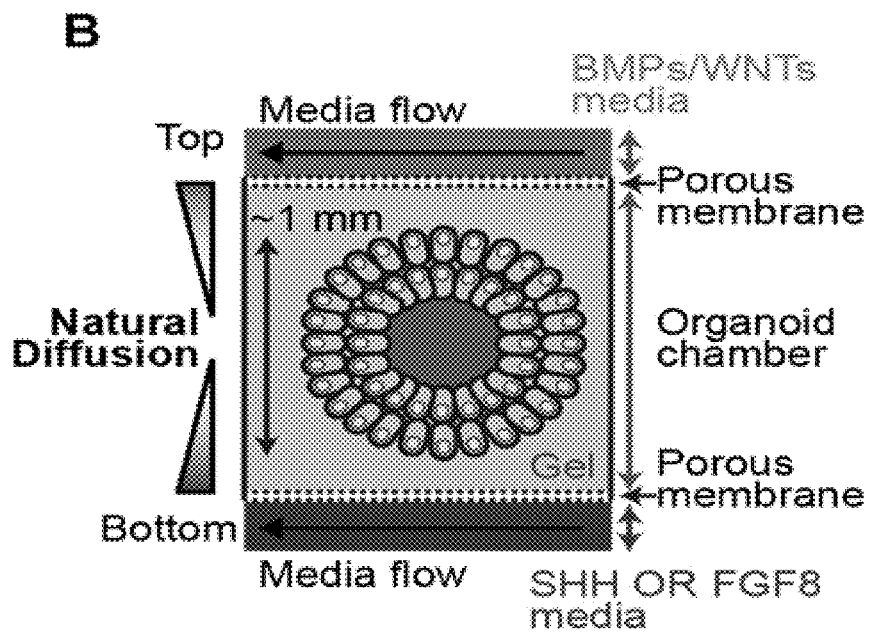
Figure 3C:
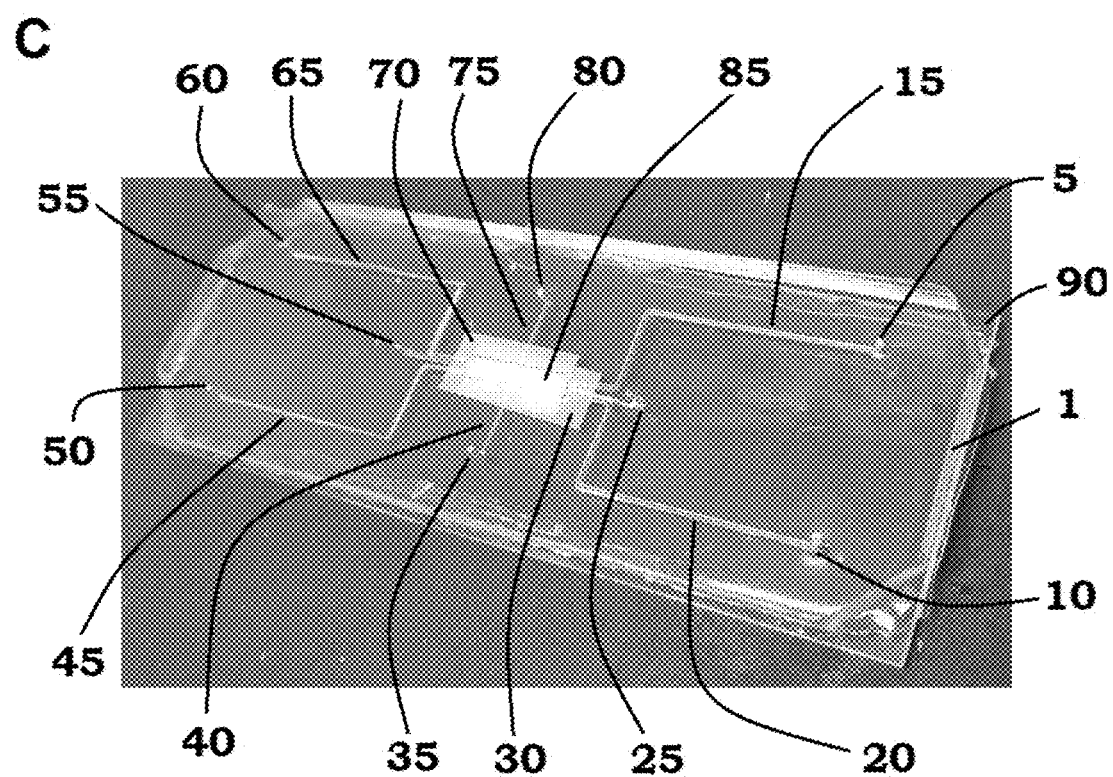
Figure 3D:
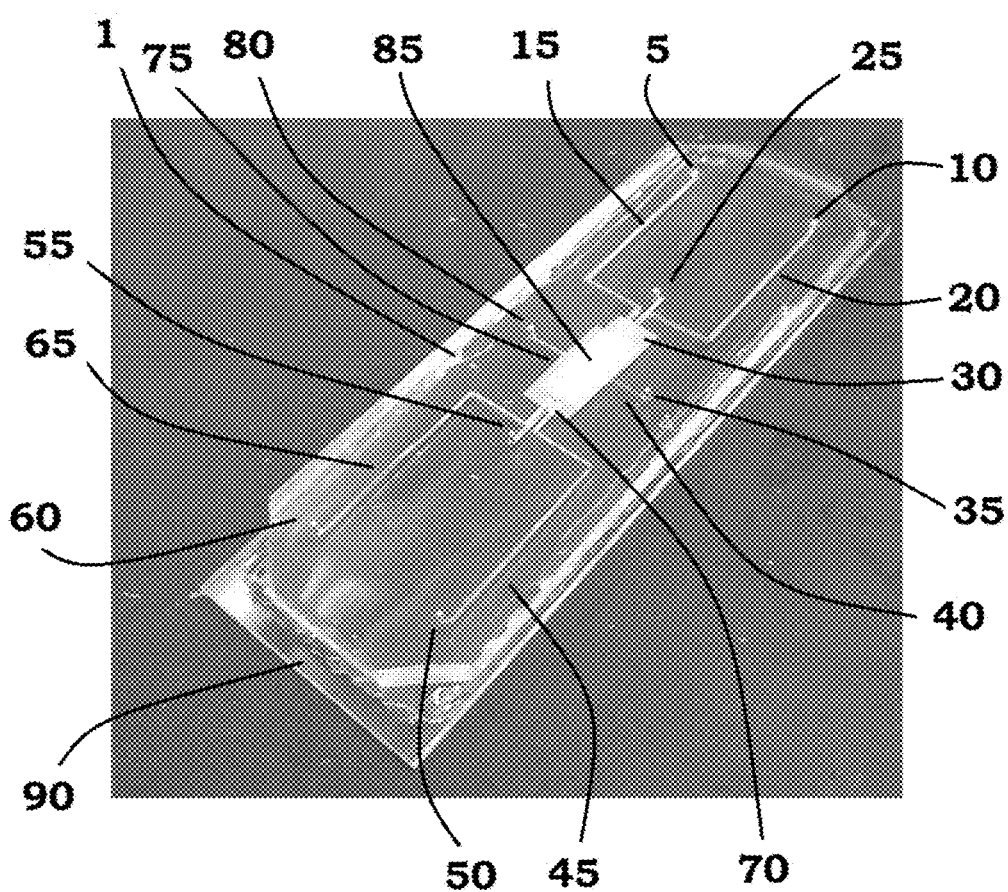
Figure 4:
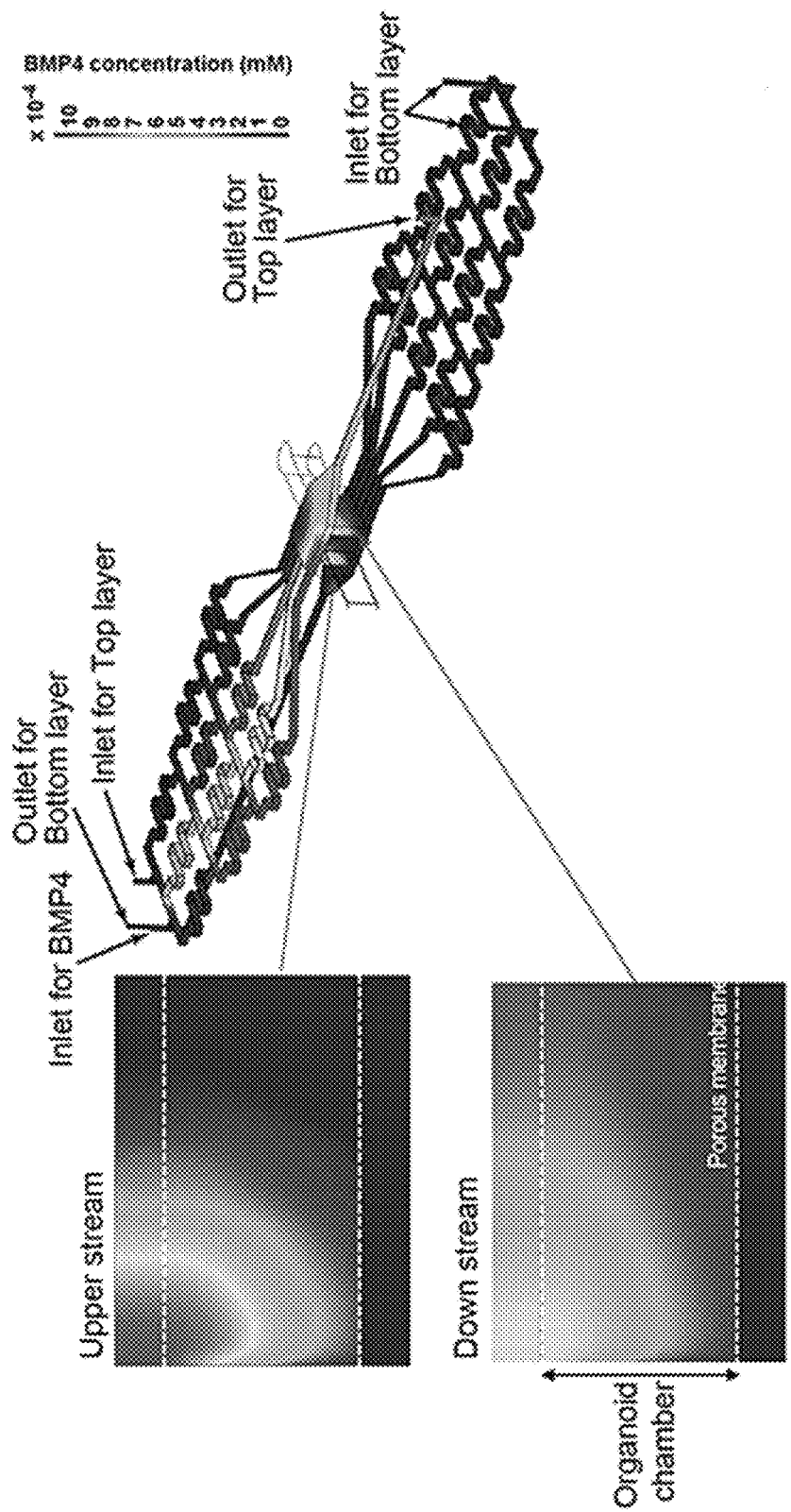
FIG. 4 provides a computational simulation of BMP4 concentration gradients in a multilayered organ-on-a-chip system disclosed herein.
Figure 5:
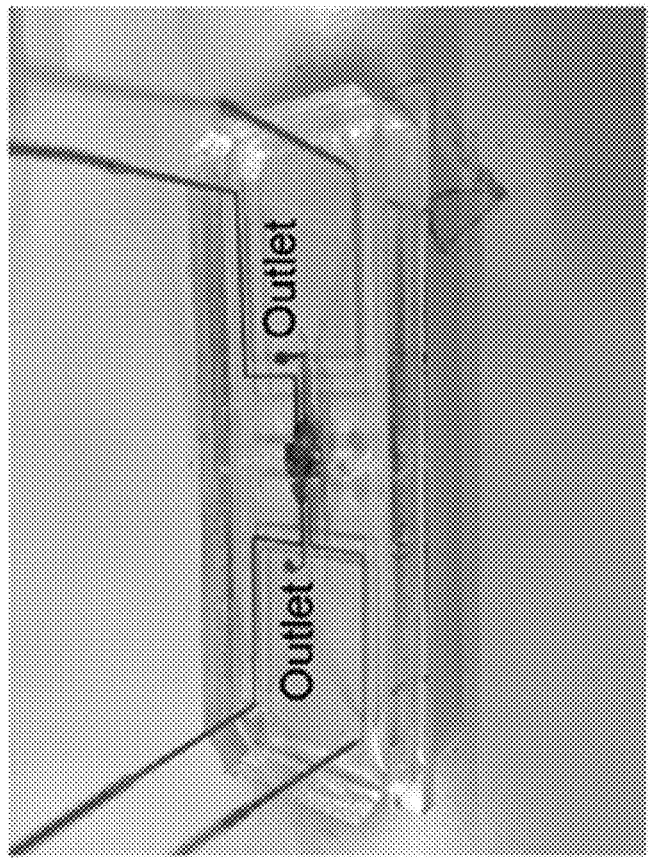
FIG. 5 demonstrates an experimental setup to introduce four colored solutions into a multilayered organ-on-a-chip system of the disclosure. Four independent syringe pumps were used to introduce corresponding solutions.
Figure 6:
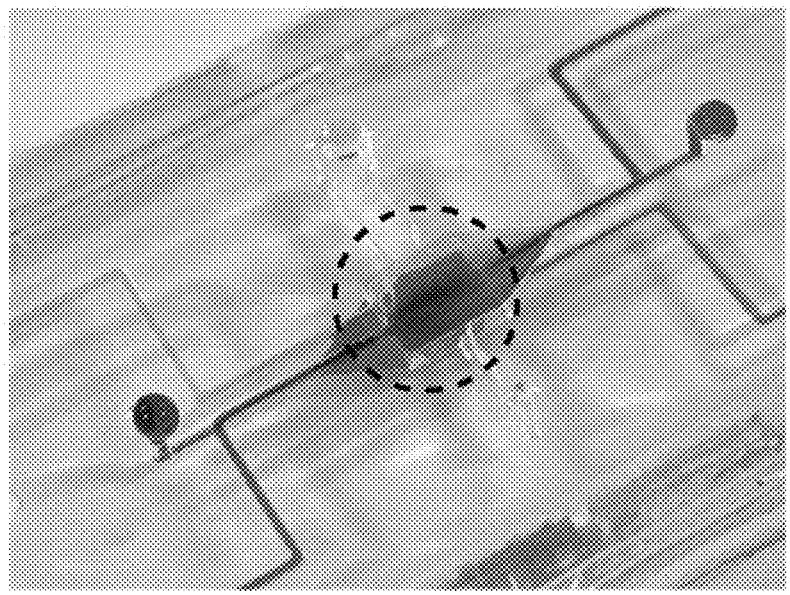
FIG. 6 provides photographs of an organoid chamber (in dashed circles) from top and bottom sides. Four colored solutions were introduced into an organoid chamber.
Figure 6:
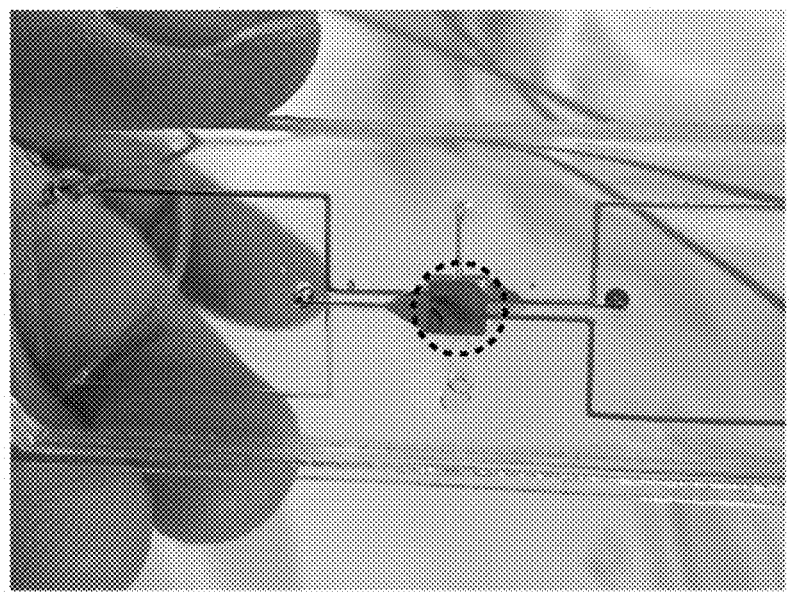
Figure 7:
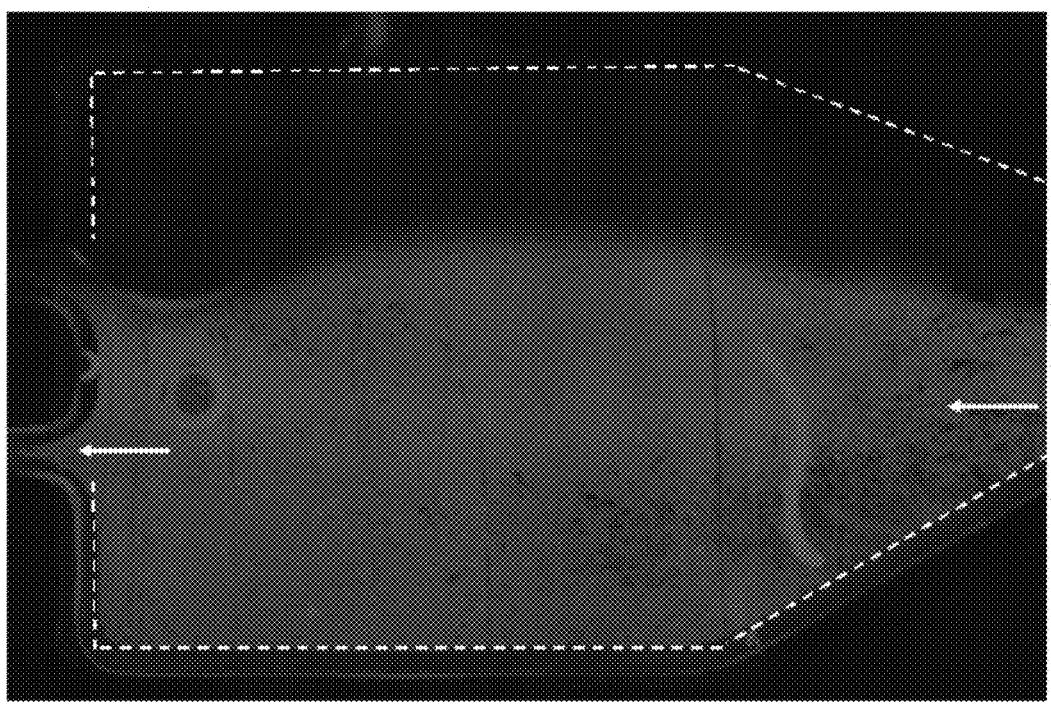
FIG. 7 presents a fluorescent micrograph of an organoid chamber (in white dashed lines) stained with red fluorescent dyes (CY5). White arrows indicate the flow direction of the fluorescent solution.
Figure 8:
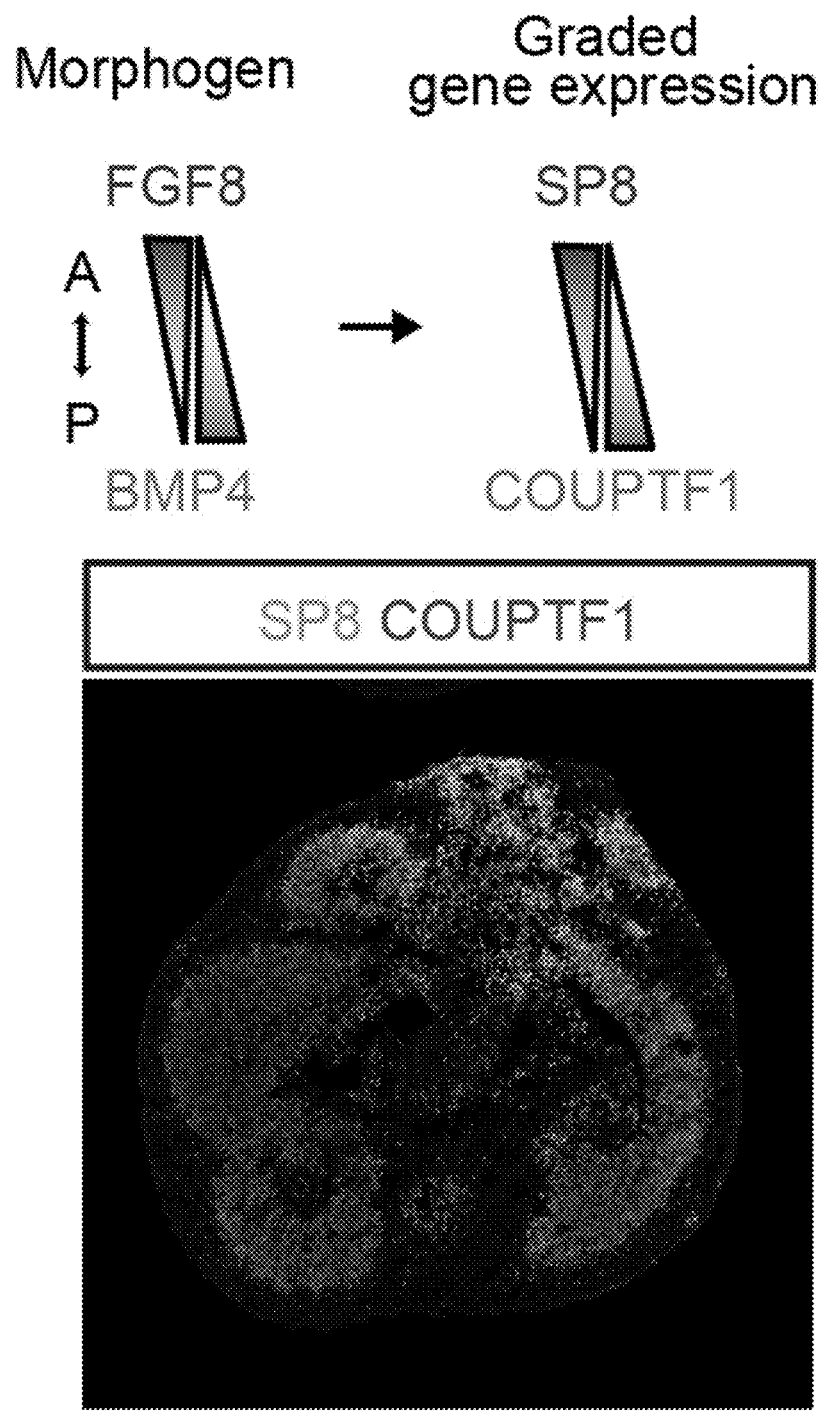
FIG. 8 demonstrates that polarized cortical organoids exhibit spatial expression of areal markers. Cortical organoids were exposed to posterior ('P') morphogen BMP4 (5 ng/mL) and anterior ('A') morphogen FGF8 (400 ng/mL) gradients. The graded expression of anterior (SP8) and posterior (COUPTF1) markers was observed.
Figure 10A:
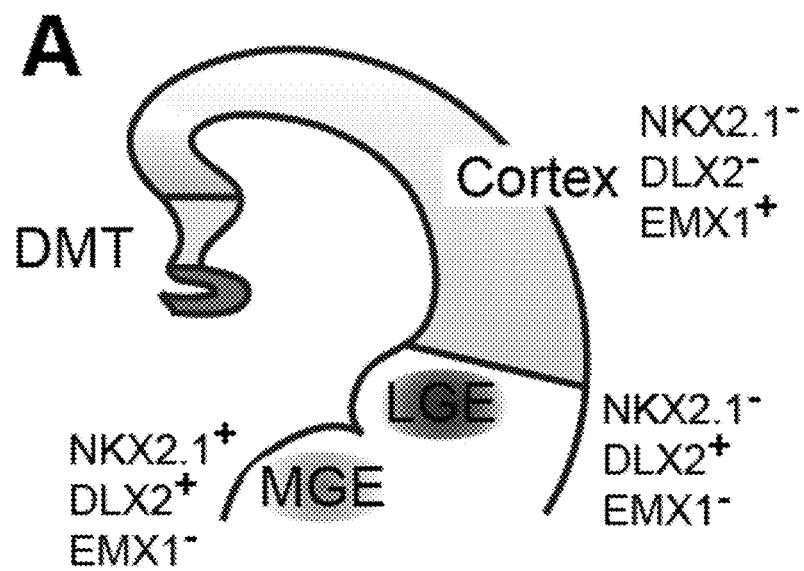
FIG. 10A-B presents the topographic organization of a telencephalon. Telencephalic organoids were exposed to ventral morphogen gradients (SHH, high affinity form, 50 ng/mL). (A) Schematic of the telencephalic regions and marker expressions in the developing human brain. (B) The ventral telencephalic regions, including the medial ganglionic eminence (MGE) and lateral ganglionic eminence (LGE), were formed adjacent to the dorsal cortical region.
Figure 10B:
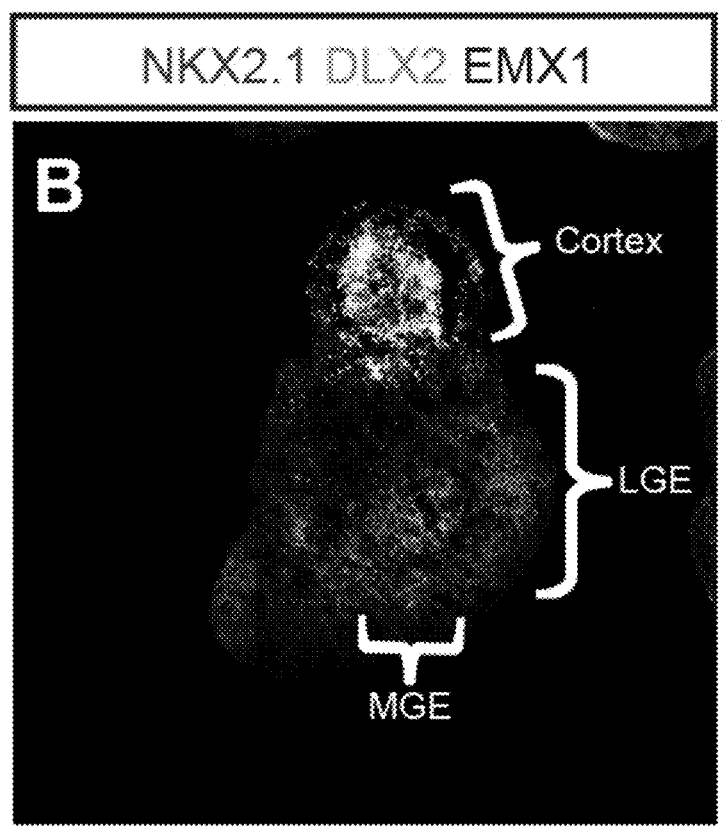

Referring to FIG. 3C-D, the figure provides photos of an exemplary multilayered organ-on-a-chip device 1 of the disclosure. The multilayered organ-on-a-chip device 1 can be fabricated using in any number of fabrication techniques known in the art, including 3D printing, lithography, molding, etching, micromachining, etc. The multilayered organ-on-a-chip device 1 can be made from any number of materials including silicon, glass, quartz, plastic, polystyrene (PS) polycarbonate (PC), polyvinyl chloride (PVC), cyclic olefin copolymer (COC), polymethylmethacrylate (PMMA), and polydimethylsiloxane (PDMS). In a particular embodiment, the multilayered organ-on-a-chip device 1 is made from PDMS. A common fabrication method for producing PDMS chip is soft lithography. In this method, liquid PDMS is mixed with a curing agent to crosslink the polymer. The amount of the curing agent used defines the hardness of the final product. The whole solution is subsequently cast over a master (typically silicon-based) mold. The master is placed in an oven at around 60° C. for 1 h to 4 h to allow crosslinking. Once cured, the PDMS is easily peeled off from the master mold. At this point, open channels are obtained, and the PDMS needs to be bonded to another surface to form enclosed channels. It can be bonded to a substrate, such as substrate 90. Substrate 90 can be made from any number of materials including silicon, glass, quartz, plastic, polystyrene (PS) polycarbonate (PC), polyvinyl chloride (PVC), cyclic olefin copolymer (COC), polymethylmethacrylate (PMMA), and polydimethylsiloxane (PDMS). In a particular embodiment, Substrate 90 is a glass, a quartz or a plastic slide or coverslip. This is done by performing a plasma treatment on the surfaces to be bonded (most common method), mechanical, or chemical bonding.

As shown, multilayered organ-on-a-chip device 1 comprises various inlet ports, outlet ports, channels, chambers, and membranes. For example, multilayered organ-on-a-chip device 1 comprises inlet port 5 and inlet port 10. Inlet port 5 and second inlet port 10 are typically sized such that they can accommodate a fluid delivery portion of reservoir, container or syringe (not shown), which can include tips, needles, nozzles and the like. First inlet port 5 is connected to microfluidic inlet channel 15. As such, fluid delivered to inlet port 5 moves down microfluidic inlet channel 15 in a directional manner to porous membrane 30. Any factors present in the fluid diffuse into organoid culture chamber 85, via porous membrane 30. Porous membrane 30 can be made from any number of materials including, but not limited to polyethylene terephthalate (PET), polycarbonate (PC), macro porous silicon, hydrophilic polytetrafluoroethylene (PTFE), polydimethylsiloxane (PDMS), cyclo olefin polymer (COP), cyclo olefin co-polymer (COC), polystyrene (PS), polyvinyl chloride (PVC) polymethylmethacrylate (PMMA) and mixed cellulose esters. Fluid in the channel above porous membrane 30 can be removed via outlet port 55. Outlet port 55 is typically sized so that it can accommodate tips, needles, nozzles and the like. Similarly, inlet port 10 is connected to microfluidic inlet channel 20. As such, fluid delivered to inlet port 10 moves down microfluidic inlet channel 20 in a directional manner to porous membrane 30. Any factors present in the fluid diffuse into organoid culture chamber 85, via porous membrane 30. Fluid in the channel above porous membrane 30 can be removed via outlet port 55. Another portion of multilayered organ-on-a-chip device 1 comprises a first inlet port 50 and inlet port 60. Inlet port 50 and second inlet port 60 are typically sized such that they can accommodate a fluid delivery portion of reservoir, container, or syringe (not shown), which can include tips, needles, nozzles and the like. First inlet port 50 is connected to microfluidic inlet channel 45. As such, fluid delivered to inlet port 50 moves down microfluidic inlet channel 45 in a directional manner to porous membrane 70. Porous membrane 70 can be made from any number of materials including, but not limited to polyethylene terephthalate (PET), polycarbonate (PC), macro porous silicon, hydrophilic polytetrafluoroethylene (PTFE), polydimethylsiloxane (PDMS), cyclo olefin polymer (COP), cyclo olefin co-polymer (COC), polystyrene (PS), polyvinyl chloride (PVC) polymethylmethacrylate (PMMA) and mixed cellulose esters. Any factors present in the fluid diffuse into organoid culture chamber 85, via porous membrane 70. Fluid in the channel below porous membrane 70 can be removed via outlet port 25. Outlet port 25 is typically sized so that it can accommodate tips, needles, nozzles and the like. Similarly, inlet port 60 is connected to microfluidic inlet channel 65. As such, fluid delivered to inlet port 60 moves down microfluidic inlet channel 65 in a directional manner to porous membrane 70. Any factors present in the fluid diffuse into organoid culture chamber 85, via porous membrane 70. Fluid in the channel below porous membrane 70 can be removed via outlet port 25. Inlet port 5, inlet port 10, inlet port 50 and inlet port 60 can have similarly sized pore apertures, or can have pore apertures having different sizes. Microfluidic inlet channel 15, microfluidic inlet channel 20, microfluidic inlet channel 45 and microfluidic inlet channel 65 can have similarly sized dimensions (e.g., similar or same lengths, diameters, slopes, etc.), or can differently sized dimensions (e.g., different lengths, diameters, slopes, etc.). Microfluidic inlet channel 15, microfluidic inlet channel 20, microfluidic inlet channel 45 and microfluidic inlet channel 65 may be coated with a hydrophobic material to prevent hydrophilic fluid retention.

The fluid in the reservoirs that can be connected to inlet port 5, inlet port 10, inlet port 50 and inlet port 60, typically comprise media with various cell, growth, cytokine and/or differentiation factors. Typically, each reservoir connected to an inlet port comprises a different concentration or types of cell, growth, cytokine and/or differentiation factors. Porous membrane 70 and porous membrane 30 are in contact with opposing sides of organoid culture chamber 85. Porous membrane 70 and porous membrane 30 can be made from a variety of materials, including but not limited to, polyethylene terephthalate (PET), polycarbonate (PC), Macro porous silicon, hydrophilic polytetrafluoroethylene (PTFE), and mixed cellulose esters. Porous membrane 70 and porous membrane 30 have a pore density typically from $5 \times 10^4$ to $5 \times 10^7$, with a pore size typically from 0.2 μm to 30 μm. Porous membrane 30 and porous membrane 70 can be made from the same materials, or from different materials. Porous membrane 30 and porous membrane 70 can have similar pore densities, or dissimilar pore densities. Porous membrane 30 and porous membrane 70 can have similar pore sizes, or dissimilar pore sizes. Use of the various ports, channels, chambers, allow for precise and consistent generation of molecular gradients by multilayered organ-on-a-chip device 1.

Inlet port 35 is connected to organoid culture chamber 85 via microfluidic channel 40. Inlet port 35 is a port that can be used to load the organoid chamber 85 with a solution comprising a thermoresponsive hydrogel and an organoid (s). Organoid chamber 85 can be loaded as follows: multilayered organ-on-a-chip device 1 is first cooled to temperature below the temperature at which the thermoresponsive hydrogel solidifies. For example, a temperature of 4° C. can be used with a PNIPAAm-PEG 3D thermoreversible hydrogel to keep the hydrogel as a liquid. The solution comprising a thermoresponsive hydrogel and an organoid(s) is introduced to inlet port 35 and travels down microfluidic channel 40 to organoid culture chamber 85. The solution is retained in organoid culture chamber 85, and the device is heated at a temperature which causes the hydrogel to solidify. For example, a temperature of 37° C. can be used to solidify the PNIPAAm-PEG 3D thermoreversible hydrogel. Excess liquid from the organoid culture chamber 85 can be removed by outlet port 80 via microfluidic channel 75. It should be noted that the organoid in organoid culture chamber 85 can be recovered by cooling multilayered organ-on-a-chip device 1 to temperature below the temperature at which the thermoresponsive hydrogel solidifies, causing the hydrogel to phase transition into a liquid. The liquid comprising the organoid can be recovered by outlet port via microfluidic channel 75.

The precise and consistent generation of molecular gradients by the multilayered organ-on-a-chip system of disclosure creates more consistent and reproducible topographic brain organoids with more cell diversity. In direct contrast, region-specific forebrain organoids are restricted to a single domain because they are induced by bath application of signaling molecules. While other groups fuse cortical and GE organoids to mimic a dorsoventral axis in vitro, such methodologies fail to fully recapitulate the in vivo tissue complex, making it impossible to study key signaling activities that are likely important for cell diversification. Furthermore, no attempt has been used by these groups to recapitulate fine arealization of the cortical organoids by generating a rostrocaudal axis and to generate ganglionic eminence organoids which also gives rise to amygdala-like identities by generating a dorsoventual axis.

The ability to generate consistent topographic organoids containing different brain regions and diverse cell types is important for accurately understanding disease pathology. In a certain embodiment, the multilayered organ-on-a-chip systems of the disclosure provide for telencephalon organoids that can be used to investigate human-specific features of brain development, function, and disease. Further, the multilayered organ-on-a-chip systems of the disclosure are readily tunable therefore, and as such are widely applicable to the study of human development or to test novel therapies for various diseases.

Organoids generated using the multilayered organ-on-a-chip systems of the disclosure can be used, for example, to screen for the efficacy and/or cytotoxicity of compounds, growth/regulatory factors, pharmaceutical compounds, and the like. Organoids generated using the multilayered organ-on-a-chip systems of the disclosure can be used can be used to examine neurological diseases and disorders by generating neuronal cells from hPSCs generated from a subject having a genetic neurological disorder. Examples of such genetic neurological disorders include, but are not limited to, Aicardi Syndrome, Alper's Disease, Batten Disease, Fabry Disease, Fahr's Syndrome, Gerstmann-Straussler-Scheinker Disease, Leigh's Disease, Lesch-Nyhan Syndrome, Menkes Disease, Moyamoya Disease, Niemann-Pick Disease, Zellweger Syndrome, Fragile X Syndrome, 2-hydroxygluraric aciduria, 3-hydroxy-3-methylglutaryl-CoA lyase deficiency, 3-methylcrotonyl-CoA carboxylase deficiency, adenylosuccinate lyase deficiency, alpha-mannosidosis, alpha-methylacyl-CoA racemase deficiency, aminoacylase 1 deficiency, arginase deficiency, argininosuccinic aciduria, aromatic L-amino acid decarboxylase deficiency, aspartylglucosaminuria, beta-ketothiolase deficiency, beta-mannosidosis, biotinidase deficiency, childhood myocerebrohepatopathy spectrum, citrullinemia, Coats plus syndrome, combined malonic and methylmalonic aciduria, dentatorubral-pallidoluysian atrophy, deoxyguanosine kinase deficiency, dihydrolipoamide dehydrogenase deficiency, dihydropyrimidine dehydrogenase deficiency, ethylmalonic encephalopathy, fucosidosis, fumarase deficiency, GABA-transaminase deficiency, galactosemia, GLUT1 deficiency syndrome, glutamate formiminotransferase deficiency, glutaric acidemia type I, glutathione synthetase deficiency, GM1 gangliosidosis, GRIN2B-related neurodevelopmental disorder, guanidinoacetate methyltransferase deficiency, hypermethioninemia, hyperprolinemia, isovaleric acidemia, L1 syndrome, Leigh syndrome, malonyl-CoA decarboxylase deficiency, MECP2-related severe neonatal encephalopathy, MEGDEL syndrome, mitochondrial complex III deficiency, mitochondrial neurogastrointestinal encephalopathy disease, molybdenum cofactor deficiency, mucolipidosis type IV, mucopolysaccharidosis type I, mucopolysaccharidosis type II, mucopolysaccharidosis type III, multiple sulfatase deficiency, myoclonic epilepsy with ragged-red fibers, N-acetylglutamate synthase deficiency, nonketotic hyperglycinemia, ornithine transcarbamylase deficiency, phosphoglycerate dehydrogenase deficiency, phosphoglycerate kinase deficiency, phosphoribosylpyrophosphate synthetase superactivity, PMM2-congenital disorder of glycosylation, prion disease, prolidase deficiency, pyruvate dehydrogenase deficiency, Schindler disease, short/branched chain acyl-CoA dehydrogenase deficiency, sialic acid storage disease, succinic semialdehyde dehydrogenase deficiency, and X-linked creatine deficiency. Organoids generated using the multilayered organ-on-a-chip systems of the disclosure can be used can be used to study neurodegenerative diseases or conditions, by use of neurodegenerative insults, including but not limited to, reperfusion injuries, protein aggregation (e.g., Alzheimer's or Parkinson associated proteins), reactions of free radicals, insufficient blood supply, glutamate excitotoxicity, and oxidative stress Depending upon the intended use for the organoids disclosed herein, various specialized cells or biological agents may be cultured with the organoids. It should be noted, that since there is no immune rejection, there is no requirement that the cells that are cultured with the organoids be from a certain genetic background or be from a certain species. It is envisaged herein, that additional specialized cells or biological agents can be used to model additional neurological disease or disorders in addition to Fragile X syndrome (FXS), in particular neurodegenerative diseases and disorders, like Parkinson's disease and Alzheimer's disease.

The disclosure further provides that the methods and devices described herein can be further defined by the following aspects (aspects 1 to 50):

1. A multilayered organ-on-a-chip system capable of generating three-dimensional molecular gradients, comprising:
   an organoid chamber configured to accommodate an organoid;
   a first porous membrane located on one side of the organoid chamber, wherein the first porous membrane allows for diffusion of a first fluid comprising cell factor(s), growth factor(s), cytokine(s) and/or differentiation factor(s) through the first porous membrane into the organoid chamber;
   a second porous membrane located on the opposite side of the organoid chamber from the first porous membrane, wherein the second porous membrane allows for diffusion of a second fluid comprising cell factor(s), growth factor(s), cytokine(s) and/or differentiation factor(s) through the second porous membrane into the organoid chamber;

a first fluid inlet channel that is contact with the organoid chamber on one end and an inlet port on the other, wherein the first fluid channel is in fluid communication with the organoid chamber via the first porous membrane;

a second fluid inlet channel that is in contact with the organoid chamber on one end and an inlet port on the other, wherein the second fluid inlet channel is in fluid communication with the organoid chamber via the second porous membrane;

a first fluid outlet channel that is contact with organoid chamber, wherein the first fluid outlet channel is in fluid communication with the organoid chamber via the first porous membrane;

a second fluid outlet channel that is contact with organoid chamber, wherein the second fluid outlet channel is in fluid communication with the organoid chamber via the second porous membrane;

wherein the first fluid inlet channel and the second fluid inlet channel are configured to flow fluids into the channels in a directional manner from the inlet ports to the organoid chamber;

wherein the first fluid outlet channel is configured to flow fluids from the organoid channel to a first outlet port in a directional manner;

wherein the second fluid outlet channel flow is configured to flow fluids from the organoid channel to a second outlet port in a directional manner;

wherein introduction of the first and second fluids into the organoid chamber via the fluid inlet channels generates a molecular gradient by natural diffusion of factors found in the fluids into the organoid channel.

2. A multilayered organ-on-a-chip system capable of generating three-dimensional molecular gradients, comprising:

an organoid chamber configured to accommodate an organoid;

a first porous membrane located on one side of the organoid chamber, wherein the first porous membrane allows for diffusion of a first fluid and a third fluid comprising cell factor(s), growth factor(s), cytokine(s) and/or differentiation factor(s) through the first porous membrane into the organoid chamber;

a second porous membrane located on the opposite side of the organoid chamber from the first porous membrane, wherein the second porous membrane allows for diffusion of a second fluid comprising cell factor(s), growth factor(s), cytokine(s) and/or differentiation factor(s) through the second porous membrane into the organoid chamber;

a first fluid inlet channel that is contact with the organoid chamber on one end and an inlet port on the other, wherein the first fluid channel is in fluid communication with the organoid chamber via the first porous membrane;

a second fluid inlet channel that is in contact with the organoid chamber on one end and an inlet port on the other, wherein the second fluid inlet channel is in fluid communication with the organoid chamber via the second porous membrane;

a third fluid inlet channel that is contact with organoid chamber on one end and an inlet port on the other, wherein the third fluid inlet channel is in fluid communication with the organoid chamber via the first porous membrane;

a first fluid outlet channel that is contact with organoid chamber, wherein the first fluid outlet channel is in fluid communication with the organoid chamber via the first porous membrane;

a second fluid outlet channel that is contact with organoid chamber, wherein the second fluid outlet channel is in fluid communication with the organoid chamber via the second porous membrane;

wherein the first fluid inlet channel, the second fluid inlet channel, and the third fluid inlet channel are configured to flow fluids into the channels in a directional manner from the inlet ports to the organoid chamber;

wherein the first fluid outlet channel is configured to flow fluids from the organoid channel to a first outlet port in a directional manner;

wherein the second fluid outlet channel flow is configured to flow fluids from the organoid channel to a second outlet port in a directional manner;

wherein introduction of the first, second and third fluids into the organoid chamber via the fluid inlet channels generates a molecular gradient by natural diffusion of factors found in the fluids into the organoid channel.

3. A multilayered organ-on-a-chip system capable of generating three-dimensional molecular gradients, comprising:

an organoid chamber configured to accommodate an organoid;

a first porous membrane located on one side of the organoid chamber, wherein the first porous membrane allows for diffusion of a first fluid comprising cell factor(s), growth factor(s), cytokine(s) and/or differentiation factor(s) through the first porous membrane into the organoid chamber;

a second porous membrane located on the opposite side of the organoid chamber from the first porous membrane, wherein the second porous membrane allows for diffusion of a second fluid and a third fluid comprising cell factor(s), growth factor(s), cytokine(s) and/or differentiation factor(s) through the second porous membrane into the organoid chamber;

a first fluid inlet channel that is contact with the organoid chamber on one end and an inlet port on the other, wherein the first fluid channel is in fluid communication with the organoid chamber via the first porous membrane;

a second fluid inlet channel that is in contact with the organoid chamber on one end and an inlet port on the other, wherein the second fluid inlet channel is in fluid communication with the organoid chamber via the second porous membrane;

a third fluid inlet channel that is contact with organoid chamber on one end and an inlet port on the other, wherein the third fluid inlet channel is in fluid communication with the organoid chamber via the second porous membrane;

a first fluid outlet channel that is contact with organoid chamber, wherein the first fluid outlet channel is in fluid communication with the organoid chamber via the first porous membrane;

a second fluid outlet channel that is contact with organoid chamber, wherein the second fluid outlet channel is in fluid communication with the organoid chamber via the second porous membrane;

wherein the first fluid inlet channel, the second fluid inlet channel, and the third fluid inlet channel are configured to flow fluids into the channels in a directional manner from the inlet ports to the organoid chamber;

wherein the first fluid outlet channel is configured to flow fluids from the organoid channel to a first outlet port in a directional manner;

wherein the second fluid outlet channel flow is configured to flow fluids from the organoid channel to a second outlet port in a directional manner;

wherein introduction of the first, second and third fluids into the organoid chamber via the fluid inlet channels generates a molecular gradient by natural diffusion of factors found in the fluids into the organoid channel.

4. A multilayered organ-on-a-chip system capable of generating three-dimensional molecular gradients, comprising:

an organoid chamber configured to accommodate an organoid;

a first porous membrane located on one side of the organoid chamber, wherein the first porous membrane allows for diffusion of a first fluid and a third fluid comprising cell factor(s), growth factor(s), cytokine(s) and/or differentiation factor(s) through the first porous membrane into the organoid chamber;

a second porous membrane located on the opposite side of the organoid chamber from the first porous membrane, wherein the second porous membrane allows for diffusion of a second fluid and a fourth fluid comprising cell factor(s), growth factor(s), cytokine(s) and/or differentiation factor(s) through the second porous membrane into the organoid chamber;

a first fluid inlet channel that is contact with the organoid chamber on one end and an inlet port on the other, wherein the first fluid channel is in fluid communication with the organoid chamber via the first porous membrane;

a second fluid inlet channel that is in contact with the organoid chamber on one end and an inlet port on the other, wherein the second fluid inlet channel is in fluid communication with the organoid chamber via the second porous membrane;

a third fluid inlet channel that is contact with organoid chamber on one end and an inlet port on the other, wherein the third fluid inlet channel is in fluid communication with the organoid chamber via the first porous membrane;

a fourth fluid inlet channel that is in contact with the organoid chamber on one end and an inlet port on the other, wherein the fourth fluid inlet channel is in fluid communication with the organoid chamber via the second porous membrane;

a first fluid outlet channel that is contact with organoid chamber, wherein the first fluid outlet channel is in fluid communication with the organoid chamber via the first porous membrane;

a second fluid outlet channel that is contact with organoid chamber, wherein the second fluid outlet channel is in fluid communication with the organoid chamber via the second porous membrane;

wherein the first fluid inlet channel, the second fluid inlet channel, the third fluid inlet channel, and the fourth fluid inlet channel are configured to flow fluids into the channels in a directional manner from the inlet ports to the organoid chamber;

wherein the first fluid outlet channel is configured to flow fluids from the organoid channel to a first outlet port in a directional manner;

wherein the second fluid outlet channel flow is configured to flow fluids from the organoid channel to a second outlet port in a directional manner;

wherein introduction of the first, second, third and fourth fluids into the organoid chamber via the fluid inlet channels generates a molecular gradient by natural diffusion of factors found in the fluids into the organoid channel.

5. The multilayered organ-on-a-chip system of any one of the preceding aspects, wherein the multilayered organ-on-a-chip system comprises polystyrene (PS) polycarbonate (PC), polyvinyl chloride (PVC), cyclic olefin copolymer (COC), polymethylmethacrylate (PMMA), and/or polydimethylsiloxane (PDMS).

6. The multilayered organ-on-a-chip system of aspect 5, wherein the multilayered organ-on-a-chip system comprises polydimethylsiloxane (PDMS).

7. The multilayered organ-on-a-chip system of any one of the preceding aspects, wherein the multilayered organ-on-a-chip system is fabricated using stereolithographic 3D-printing techniques and solution cast-molding processes.

8. The multilayered organ-on-a-chip system of aspect 7, wherein the molds for the fluid inlet and/or outlet channels are produced using a 3D printer.

9. The multilayered organ-on-a-chip system of any preceding aspect, wherein the organoid chamber has the dimensions of a cube, a cylinder, a sphere, or a cuboid.

10. The multilayered organ-on-a-chip system of any one of the preceding aspects, wherein the organoid chamber comprises at least one wall, a top surface and a bottom surface.

11. The multilayered organ-on-a-chip system of aspect 10, wherein the first porous membrane defines the top surface of the organoid chamber.

12. The multilayered organ-on-a-chip system of aspect 10 or aspect 11, wherein the second porous membrane defines the bottom surface of the organoid chamber.

13. The multilayered organ-on-a-chip system of any one of the preceding aspects, wherein the organoid chamber is internally accessible by being comprised of two joinable sections, wherein one section is configured to comprise the first porous membrane, and the other section is configured to comprise the second porous membrane, and wherein an organoid can be placed within the organoid chamber prior to the joining of the sections.

14. The multilayered organ-on-a-chip system of aspect 13, wherein the two sections are joined together by clamps, fixtures, screws, or clips.

15. The multilayered organ-on-a-chip system of aspect 13 or aspect 14, wherein the two sections comprise a top section and a bottom section.

16. The multilayered organ-on-a-chip system of any one of aspects 13 to 15, wherein the thickness of the two sections is similar or identical.

17. The multilayered organ-on-a-chip system of any one of aspects 13 to 15, wherein the thickness of one section is between 5× to 10× thicker than the other section.

18. The multilayered organ-on-a-chip system of aspect 17, wherein a top section is 5× to 10× thicker than a bottom section.

19. The multilayered organ-on-a-chip system of any one of aspects 13 to 18, wherein the first porous membrane is fixed to one section and the second porous membrane is fixed to the other section.
20. The multilayered organ-on-a-chip system of any one of the preceding aspects, wherein the first porous membrane is comprised of a material selected from polyethylene terephthalate (PET), polycarbonate (PC), macro porous silicon, hydrophilic polytetrafluoroethylene (PTFE), polydimethylsiloxane (PDMS), cyclo olefin polymer (COP), cyclo olefin co-polymer (COC), polystyrene (PS), polyvinyl chloride (PVC) polymethylmethacrylate (PMMA) and/or mixed cellulose esters.
21. The multilayered organ-on-a-chip system of aspect 20, wherein the first porous membrane is comprised of PET.
22. The multilayered organ-on-a-chip system of any one of the preceding aspects, wherein the second porous membrane is comprised of a material selected from polyethylene terephthalate (PET), polycarbonate (PC), macro porous silicon, hydrophilic polytetrafluoroethylene (PTFE), polydimethylsiloxane (PDMS), cyclo olefin polymer (COP), cyclo olefin co-polymer (COC), polystyrene (PS), polyvinyl chloride (PVC) polymethylmethacrylate (PMMA) and/or mixed cellulose esters.
23. The multilayered organ-on-a-chip system of aspect 22, wherein the second porous membrane is comprised of PET.
24. The multilayered organ-on-a-chip system of any one of the preceding aspects, wherein the first porous membrane has a pore size from 0.1 μm to 1 μm.
25. The multilayered organ-on-a-chip system of aspect 24, wherein the first porous membrane has a pore size from 0.2 μm to 0.5 μm.
26. The multilayered organ-on-a-chip system of any one of the preceding aspects, wherein the second porous membrane has a pore size from 0.1 μm to 1 μm.
27. The multilayered organ-on-a-chip system of aspect 26, wherein the second porous membrane has a pore size from 0.2 μm to 0.5 μm.
28. The multilayered organ-on-a-chip system of any one of the preceding aspects, wherein the organoid chamber comprises a primitive neuroepithelial organoid embedded in a hydrogel.
29. The multilayered organ-on-a-chip system of aspect 28, wherein the hydrogel is a thermoreversible hydrogel.
30. The multilayered organ-on-a-chip system of aspect 29, wherein the thermoreversible hydrogel comprises poly(N-isopropylacrylamide) (PNIPAAm or PNIPAM) and poly(ethylene glycol) (PEG) based hydrogel, or aPNIPAAm and hyaluronic acid (HA) based hydrogel.
31. The multilayered organ-on-a-chip system of any one of aspects 28 to 30, wherein the primitive neuroepithelial organoid is neurally differentiated from hPSCs, iPSCs, or ESCs.
32. The multilayered organ-on-a-chip system of aspect 31, wherein the hPSCs, iPSCs, or ESCs are generated from the cells of a human subject.
33. The multilayered organ-on-a-chip system of aspect 31 or aspect 32, wherein the hPSCs, iPSCs, or ESCs are generated from cells of a subject that has a genetic neurological disorder.
34 The multilayered organ-on-a-chip system of aspect 33, wherein the genetic neurological disorder is selected from the group consisting of Aicardi Syndrome, Alper's Disease, Batten Disease, Fabry Disease, Fahr's Syndrome, Gerstmann-Straussler-Scheinker Disease, Leigh's Disease, Lesch-Nyhan Syndrome, Menkes Disease, Moya Moya Disease, Niemann-Pick Disease, Zellweger Syndrome, Fragile X Syndrome, 2-hydroxygluraric aciduria, 3-hydroxy-3-methylglutaryl-CoA lyase deficiency, 3-methylcrotonyl-CoA carboxylase deficiency, adenylosuccinate lyase deficiency, alpha-mannosidosis, alpha-methylacyl-CoA racemase deficiency, aminoacylase 1 deficiency, arginase deficiency, argininosuccinic aciduria, aromatic L-amino acid decarboxylase deficiency, aspartylglucosaminuria, beta-ketothiolase deficiency, beta-mannosidosis, biotinidase deficiency, childhood myocerebrohepatopathy spectrum, citrullinemia, Coats plus syndrome, combined malonic and methylmalonic aciduria, dentatorubral-pallidoluysian atrophy, deoxyguanosine kinase deficiency, dihydrolipoamide dehydrogenase deficiency, dihydropyrimidine dehydrogenase deficiency, ethylmalonic encephalopathy, fucosidosis, fumarase deficiency, GABA-transaminase deficiency, galactosemia, GLUT1 deficiency syndrome, glutamate formiminotransferase deficiency, glutaric acidemia type I, glutathione synthetase deficiency, GM1 gangliosidosis, GRIN2B-related neurodevelopmental disorder, guanidinoacetate methyltransferase deficiency, hypermethioninemia, hyperprolinemia, isovaleric acidemia, L1 syndrome, Leigh syndrome, malonyl-CoA decarboxylase deficiency, MECP2-related severe neonatal encephalopathy, MEGDEL syndrome, mitochondrial complex III deficiency, mitochondrial neurogastrointestinal encephalopathy disease, molybdenum cofactor deficiency, mucolipidosis type IV, mucopolysaccharidosis type I, mucopolysaccharidosis type II, mucopolysaccharidosis type III, multiple sulfatase deficiency, myoclonic epilepsy with ragged-red fibers, N-acetylglutamate synthase deficiency, nonketotic hyperglycinemia, ornithine transcarbamylase deficiency, phosphoglycerate dehydrogenase deficiency, phosphoglycerate kinase deficiency, phosphoribosylpyrophosphate synthetase superactivity, PMM2-congenital disorder of glycosylation, prion disease, prolidase deficiency, pyruvate dehydrogenase deficiency, Schindler disease, short/branched chain acyl-CoA dehydrogenase deficiency, sialic acid storage disease, succinic semialdehyde dehydrogenase deficiency, and X-linked creatine deficiency.
35. The multilayered organ-on-a-chip system of aspect 34, wherein the genetic neural disorder is Fragile X Syndrome.
36. The multilayered organ-on-a-chip system of any one of the preceding aspects, wherein the first fluid comprises different types and/or different concentrations of cell, growth, cytokine and/or differentiation factors than the second fluid.
37. The multilayered organ-on-a-chip system of any one of the preceding aspects, wherein the first fluid comprises high concentrations of dorsalizing/caudalizing factors.
38. The multilayered organ-on-a-chip system of aspect 37, wherein the dorsalizing/caudalizing factors is BMP4 and WNT3A.
39. The multilayered organ-on-a-chip system of any one of the preceding aspects, wherein the second fluid comprises high concentrations of a ventralizing or a rostralizing factor.

40. The multilayered organ-on-a-chip system of aspect 39, wherein the ventralizing or rostralizing factor is SHH or FGF8.

41. The multilayered organ-on-a-chip system of any one of the preceding aspects, wherein the introduction of the fluids generates a multi-concentration gradient that promotes the further differentiation of the primitive neuroepithelial organoid into a topographic neural organoid.

42. The multilayered organ-on-a-chip system of aspect 41, wherein the topographic neural organoid is a brain organoid, a cortical organoid, or a ganglionic eminence organoid.

43. The multilayered organ-on-a-chip system of aspect 42, wherein the brain organoid has topographic organization of the choroid plexus, hippocampal, cortical, antihem, and/or lateral and media ganglionic eminence regions.

44. The multilayered organ-on-a-chip system of aspect 42, wherein the brain organoid is a brain organoid derived from cells of a subject that has a genetic neurological disorder.

45. The multilayered organ-on-a-chip system of aspect 44, wherein the brain organoid is a Fragile X Syndrome brain organoid.

46. A method for screening drugs or agents for their effects on the brain organoid of aspect 44 or aspect 45, comprising:
contacting the brain organoid with one or more drugs or agents;
assessing the effects of the one or more drugs or agents on the brain organoid activity and/or function.

47. The method of aspect 46, wherein the brain organoid is contacted with the one or more drugs or agents by introducing one or more drugs or agents into the one or more of the fluid inlet channels.

48. The method of aspect 46, wherein the network activities in the cortical region of the brain organoid are assessed.

49. The method of any one of aspects 46 to 48, wherein the one or more drugs or agents are drugs or agents that are used, or suspected of having use for treating neurological disorders or conditions.

50. The method of any one of aspects 46 to 49, wherein the one or more drugs or agents are selected from Acamprosate, Adrenaline, Agomelatine, Almotriptan, Amantadine, Amisulpride, Amitriptyline, Apomorphine, Aripiprazole, Asenapine, Atomoxetine, Baclofen, Botulinum toxin type A, Bromocriptine, Buprenorphine, Buspirone, Cabergoline, Carbamazepine, Chlordiazepoxide, Chlorpromazine, Citalopram, Clobazam, Clomethiazole, Clomipramine, Clozapine, Co-beneldopa, Co-careldopa, Dantrolene, Dexamfetamine, Diazepam, Divalproex, Donepezil, Doxepin, Duloxetine, Eletriptan, Entacapone, Escitalopram, Eslicarbazepine, Ethosuximide, Fingolimod, Fluoxetine, Flupentixol, Fluphenazine, Fluvoxamine, Frovatriptan, Gabapentin, Galantamine, Haloperidol, Hydromorphone, Imipramine, Lacosamide, Lamotrigine, Levetiracetam, Levomepromazine, Lisdexamfetamine, Lithium, Lofepramine, Loprazolam, Lorazepam, Lormetazepam, Lurasidone, Melatonin, Memantine, Methylphenidate, Mianserin, Midodrine, Mirtazapine, Moclobemide, Modafinil, Morphine, Naratriptan, Neostigmine, Nitrazepam, Nortriptyline, Olanzapine, Orlistat, Orphenadrine, Oxazepam, Oxcarbazepine, Oxycodone, Paliperidone, Paroxetine, Perampanel, Pergolide, Pericyazine, Phenobarbital, Phenytoin, Piracetam, Pizotifen, Pramipexole, Pregabalin, Primidone, Prochlorperazine, Procyclidine, Pyridostigmine, Quetiapine, Rasagiline, Reboxetine, Risperidone, Risperidone, Rivastigmine, Rizatriptan, Ropinirole, Rotigotine, Rufinamide, Selegiline, Sertraline, Sodium oxybate, Sodium valproate, Sulpiride, Sumatriptan, Temazepam, Tetrabenazine, Tiagabine, Tizanidine, Tolcapone, Topiramate, Trazodone, Trihexyphenidyl, Trimipramine, Valproate, Venlafaxine, Vigabatrin, Vortioxetine, Zolmitriptan, Zolpidem, Zonisamide, Zopiclone, and/or Zuclopenthixol.

For use in the therapeutic or biological applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise a multilayered organ-on-a-chip system described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The following examples are intended to illustrate but not limit the disclosure. While they are typical of those that might be used, other procedures known to those skilled in the art may alternatively be used.

EXAMPLES

Pluripotent stem cell culture and organoid differentiation. hPSC lines H9, UCLA1, hIPS2 and XFiPS are obtained and maintained on 0.1% gelatin-coated plates with irradiated mouse embryonic feeders in DMEM/F12 (Hyclone) with 20% Knockout Serum Replacement (KSR: Invitrogen), MEM Non-Essential Amino Acids (NEAA: Invitrogen), GlutaMAX (Invitrogen), 0.1 mM β-mercaptoethanol (Invitrogen), 100 µg/ml Primocin (InvivoGen), and 10 ng/mL of FGF2 (Invitrogen). hPSC are maintained at 5% $CO_2$ at 37° C. with daily media change, and are passaged every 6 days at 1:3-1:6 using StemPro EZ Passage tool (Invitrogen). Experiments are performed on cells between passages 40-80 for H9, UCLA1, and hIPS2, and between passages 10-20 for XFiPS.

Cortical organoid differentiation is performed as described in Kadoshima et al., (Proc Natl Acad Sci USA 110:20284-20289 (2013)) with several modifications. Briefly, hPSC are dissociated to single cells and plated into low attachment V-bottom 96-well plates (Sumitomo Bakelite, #MS-9096V) to form aggregates in GMEM (Invitrogen), 20% KSR, NEAA, 100 µg/mL Primocin, 0.1 mM β-mercaptoethanol, sodium pyruvate (Invitrogen), and 20 µM ROCK inhibitor (BioPioneer) without Wnt and TGFβ inhibitors. Half of the media is changed every 2-3 days. ROCK inhibitor is removed after 6 days. Aggregates are then transferred to a hyperoxygenated incubator at 5% $CO_2$ and 40% $O_2$ and maintained in DMEM/F12 with N2 (Invitrogen), GlutaMAX, Chemically Defined Lipid Concentrate (CDLC: Invitrogen), and 0.4% methylcellulose (Sigma). Culture media is completely changed every 2-3 days thereafter. On day 35, organoids are cut in half using Vannas spring scissors (Fine Science Tools) and media changed to N2B27 media containing DMEM/F12 supplemented with N2, GlutaMAX, CDLC, 0.4% methylcellulose, B27 without vitamin A (Invitrogen), 1% Growth Factor Reduced Matrigel (Fisher Scientific, #CB-40230), and 5 µg/mL heparin (Sigma). For the FBS method, 10% FBS (Invitrogen) is used in place of B27 without vitamin A. On day 56, organoids are cut in half and transferred to oxygen permeable dishes (Lumox, Sarstedt) containing N2B27 media. Organoids are subsequently cut in half every 2 weeks and routinely sustained for up to 150 days. For STAT3 activation, Leukemia Inhibitory Factor (LIF, Millipore) is added at 2,000 U/mL from D35 onward. At the end of the experiments, organoids are processed for immunohistochemical and RNA analyses.

The differentiation of basal ganglionic eminence (GE) organoids was based upon the method used for cortical organoid differentiation. From day 15-21, smoothened agonist (SAG, Millipore) was added to the media to activate sonic hedgehog signaling (200 nM for the lateral ganglionic eminence organoid; 1 uM for the medial ganglionic eminence).

hPSC maintenance and telencephalic organoid differentiation. hPSCs under MEF-supported conditions (Millipore, PMEF-CF) are maintained as described above. hPSCs under feeder-free conditions are maintained with mTeSRTM1 (Stemcell Technologies, 85850) or Essential 8 medium (E8, ThermoFisher, A15117001) and where specified on hESC-qualified Matrigel substrate (Fisher Scientific, 08-774-552). Every 3-5 days, hPSCs are passaged at a 1:10-1:15 dilution with partial dissociation using ReLeSR (Stemcell Technologies, 5872). For the 4G method, hPSCs are preconditioned with growth factors for 3-4 days one day after passage. Growth factor concentrations are as follows: BMP4 (0.1 ng/mL, Invitrogen, PHC9534), TGFβ1 (0.1 ng/mL, R&D Systems, 240-B), ACTIVIN A (10-20 ng/mL, Peprotech, 120-14P), and NODAL (50 ng/mL, R&D Systems, 3218-ND) or TGFβ3 (1 ng/mL, R&D Systems, 8420-B3). Cerebral and basal ganglionic eminence (GE) organoid formation is performed as described as above. Of note, KnockOut Serum Replacement (KSR) is known to affect differentiation efficiency and the differentiation protocol using the same KSR lot (KSR, Invitrogen, 10828010 and 10828028) lot (1670543) is utilized. For the formation of dorsomedial telencephalic (DMT) organoids, a modified version of the methods described in Sakaguchi et al. (Nat Commun 6:8896 (2015)) is used. From day 18-24, BMP4 (6.5 ng/mL, Invitrogen, P2026055) and GSK3 inhibitor (3 µM of CHIR 99021, Fisher Scientific, 442310) are added with DMEM/F-12 (Hyclone) supplemented with 1% N2 (Invitrogen), 1% chemically defined lipid concentrate (CDLC, Invitrogen), 10% fetal bovine serum (FBS qualified source US region, Invitrogen, 10437028) under 40% 02 and 5% $CO_2$ conditions at 37° C. On day 42, DMT organoids are cut in half and the base media is changed to Neurobasal medium (Invitrogen), supplemented with 1% N2 (Invitrogen), 1% CDLC, 10% FBS, 2% B-27 supplement without vitamin A (Invitrogen), GlutaMAX (Invitrogen), 100 µg/mL of Primocin (InvivoGen). After day 42, DMT organoids are cut into half every two weeks. From day 56, DMT organoids are cultured in Lumox dishes (SARSTEDT). Media is subsequently changed every 2-3 days until the organoids were collected.

Primed hPSC maintenance, primed to naïve conversion, and naïve hPSC maintenance. Primed hPSCs are maintained in primed media consisting of 20% KSR in DMEM/F12 supplemented with 1× nonessential amino acids, 2 mM L-Glutamine, 0.5× Penicillin/Streptomycin (all from Invitrogen), 0.1 mM β-mercaptoethanol (Sigma-Aldrich), and 4 ng/mL FGF2 (Peprotech). Primed hPSCs are cultured on CF-1 irradiated MEFs and passaged every 4-5 days with collagenase IV (ThermoFisher Scientific) at 37° C. for 5 minutes, followed by manual dissociation by pipetting. Primed hPSCs are converted to naive H9 as previously described in Guo et al. (Development 144:2748-2763 (2017)). Briefly, primed hPSCs are dissociated into single cells with Accutase and $2 \times 10^5$ cells per 6-well are plated in primed media with 10 µM Y-27632 onto MEFs seeded at a density of $2 \times 10^6$ cells per 6-well plate. The following day (day 1), media is changed to cRM-1, which comprises N2B27 basal media supplemented with 1 µM PD0325901 (Cell Guidance Systems), 20 ng/mL human LIF (Millipore) and 1 mM Valproic Acid (Sigma-Aldrich). On day 4, the media is switched to cRM-2 consisting of N2B27 basal media supplemented with 1 µM PD0325901 (Cell Guidance Systems), 20 ng/mL human LIF (Millipore), 2 µM Go6983 (Tocris) and 2 µM XAV939. From day 11 onwards, converted naive cells are cultured in t2iLGo media. Cells are passaged on day 5, day 10, and every 4-5 days subsequently. Homogenous naive hPSC lines are obtained after 4 passages in t2iLGo media. Naive hPSCs are subsequently maintained in t2iLGo media (Takashima et al., 2014) comprising a 1:1 mixture of DMEM/F12 and Neurobasal, 0.5% N2 supplement, 1% B27 supplement, lx nonessential amino acids, 2 mM L-Glutamine, 0.5× Penicillin/Streptomycin (all from ThermoFisher Scientific), 0.1 mM β-mercaptoethanol (Sigma-Aldrich) (N2B27 basal media) supplemented with 1 µM PD0325901 (Cell Guidance Systems), 1 µM CHIR99021 (Cell Guidance Systems), 20 ng/mL human LIF (Millipore) and 2 µM Go6983 (Tocris) on CF-1 irradiated MEFs. Naive hPSCs were passaged every 4 days with Accutase (ThermoFisher Scientific) at 37° C. for 5 minutes. Naive hPSCs between passages 5-7 were used for organoid experiments. All H9 ESCs were cultured in 5% 02, 5% $CO_2$ at 37° C. and subject to daily media changes.

Tissue processing and immunohistochemistry. Brain organoids are fixed, cryoprotected, embedded, frozen, and cryosectioned as described in Watanabe et al. (2017). Sectioned tissues are collected onto Superfrost Plus slides (Fisher Scientific) and blocked for 30 minutes in PBS with 1% heat inactivated equine serum (Hyclone), 0.1% Triton X-100, and 0.05% sodium azide and incubated in primary antibodies (see Table S6) in the blocking solution overnight at 4° C. After three washes in PBST (0.1% Triton X-100), tissue is incubated with secondary antibodies for one hour at room temperature. After three washes, tissue is mounted in ProLongR Diamond (Invitrogen) with coverslips and stored in the dark at 4° C. prior to imaging.

Microscopic imaging. Confocal images are acquired using a Zeiss LSM 780 or 800 microscope equipped with a motorized stage and Zen black or blue software. Tiled images are assembled using the Zen Tiles with the multi-focus function. For brightfield imaging, a Zeiss Axio Observer D1 microscope is used. All images are compiled in Adobe Photoshop or ImageJ, with image adjustment applied to the entire image and restricted to brightness, contrast, and levels.

RNA isolation, processing, and RNA-sequencing analyses. Samples are lysed in QIAzol and RNA extracted following manufacturer's instructions (Qiagen, miRNeasy Micro Kit). For RNA-sequencing analyses, hPSCs, particularly H9 hESCs and XFiPSCs, are collected with 3 replicates (3 independent experiments, 4 conditions, 12 samples total) for feeder-dependent and feeder-independent conditions. RNA integrity is confirmed with the Agilent 2200 TapeStation (RIN>8). cDNA libraries are generated using TruSeq with Ribo-Zero Gold (Illumina) and sequenced using an Illumina HiSeq 4000 system, yielding about 50 million reads per sample. A paired end RNA-sequencing with 75 bp reads is utilized. STAR (version 2.4.0j) is used to align RNA reads to the human genome (GRCh37/hg19). All samples have greater than 80% read alignment. This genome version is also used for subsequent read quantification (exon counts) with HTSeq (version 0.6.1p1). QC statistics are obtained per sample using Picard tools (broadinstitute.github.io/picard) to be used in downstream analysis to account for technical variation in gene expression data. QC statistics collected included: AT/GC dropout, read duplication rate, GC bias, read depth, percentage of different genomic regions covered (exons, introns, UTRs, etc.), 5' end sequencing bias etc. Differential gene expression was performed in R (r-project.org) as follows using HTSeq exon and lncRNA counts. First, genes are filtered such that only genes with a count greater than 10 in at least 80% of samples are retained. The DESeq2 package is then used to both normalized gene expression data (using varianceStabilizingTransform) and to calculate differentially expressed genes between conditions of interest. Based on the association of Picard QC statistics and other covariates with top normalized gene expression principal components, the covariates of condition (hPSC type and feeder type), RIN, RNA concentration, and the first principal component of the Picard sequencing statistics are included as linear model covariates during differential gene expression calculation. Groups of differentially expressed genes are identified as either significantly up- or down-regulated between conditions with a false discovery rate (FDR)<5%. Groups of differentially expressed genes between conditions are subjected to the following enrichment analyses. Gene ontology analysis is performed using Metascape online software (metascape.org). Cell type markers of the naive and primed states are also used to find any enrichment in groups of differentially expressed genes using the pSI R package. Protein-protein interaction enrichment is established using DAPPLE.

Quantitative PCR. Reverse Transcriptase qPCR (RT-qPCR) is performed as described in Watanabe et al. (2017). Briefly, total RNA is extracted using a RNeasy Mini or miRNeasy Mini Kit (Qiagen) and >500 ng of total RNA is used for cDNA synthesis for each sample, using the SuperScript IV First-Strand Synthesis System (Invitrogen). For RT-qPCR reaction, LightCycler 480 SYBR Green I Master Mix and exon-spanning primer pairs listed below are used with synthesized cDNA. All reactions are performed using a Roche LightCycler 480 real-time PCR system in triplicates, and relative expression levels are determined by normalizing the crossing points to the internal reference gene β-ACTIN.

```
(amplicon size 51 bp)
                                     (SEQ ID NO: 1)
Fwd 5'-AGTTCTCCAGCTCGCTCAGC-3', (SEQ ID NO: 2)
Rev 5'-GGAACCATATCTTCACCTGCGT-3';

NANOG (amplicon size 116 bp)
                                     (SEQ ID NO: 3)
Fwd 5'-TTTGTGGGCCTGAAGAAAACT-3', (SEQ ID NO: 4)
Rev 5'-AGGGCTGTCCTGAATAAGCAG-3';

NKX2.1 (amplicon size 68 bp)
                                     (SEQ ID NO: 5)
Fwd 5'-AGCACACGACTCCGTTCTC-3', (SEQ ID NO: 6)
Rev 5'-GCCCACTTTCTTGTAGCTTTCC-3';

OCT4 (amplicon size 156 bp)
                                     (SEQ ID NO: 7)
Fwd 5'-GGAGAAGCTGGAGCAAAAC-3', (SEQ ID NO: 8)
Rev 5'-ACCTTCCCAAATAGAACCCC-3';

OLIG2 (amplicon size 90)
                                     (SEQ ID NO: 9)
Fwd 5'-ATAGATCGACGCGACACCAG-3', (SEQ ID NO: 10)
Rev 5'-ACCCGAAAATCTGGATGCGA-3';

OTX2 (amplicon size 154 bp)
                                     (SEQ ID NO: 11)
Fwd 5'-AGAGGACGACGTTCACTCG-3', (SEQ ID NO: 12)
Rev 5'-TCGGGCAAGTTGATTTTCAGT-3';

PV (amplicon size 96 bp)
                                     (SEQ ID NO: 13)
Fwd 5'-AAGAGTGCGGATGATGTGAAG-3', (SEQ ID NO: 14)
Rev 5'-GCCTTTTAGGATGAATCCCAGC-3';

SOX2 (amplicon size 155 bp)
                                     (SEQ ID NO: 15)
Fwd 5'-GCCGAGTGGAAACTTTTGTCG-3', (SEQ ID NO: 16)
Rev 5'-GGCAGCGTGTACTTATCCTTCT-3';

SST (amplicon size 108 bp)
                                     (SEQ ID NO: 17)
Fwd 5'-ACCCAACCAGACGGAGAATGA-3', (SEQ ID NO: 18)
Rev 5'-GCCGGGTTTGAGTTAGCAGA-3';

TFAP2C (amplicon size 114 bp)
                                     (SEQ ID NO: 19)
Fwd 5'-CTGTTGCTGCACGATCAGACA-3', (SEQ ID NO: 20)
Rev 5'-CTCAGTGGGGTTCATTACGGC-3';
```

-continued

```
TFCP2L1 (amplicon size 245 bp)
                                  (SEQ ID NO: 21)
Fwd 5'-ATACCAGCCGTCCTATGAAACC-3', (SEQ ID NO: 22)
Rev 5'-ACTGCGAGAACCTGTTGCG-3';

TGFβ1 (amplicon size 209 bp)
                                  (SEQ ID NO: 23)
Fwd 5'-CTAATGGTGGAAACCCACAACG-3', (SEQ ID NO: 24)
Rev 5'-TATCGCCAGGAATTGTTGCTG-3';

TGFβ3 (amplicon size 114 bp)
                                  (SEQ ID NO: 25)
Fwd 5'-ACTTGCACCACCTTGGACTTC-3', (SEQ ID NO: 26)
Rev 5'-GGTCATCACCGTTGGCTCA-3';

TTR (amplicon size 229 bp)
                                  (SEQ ID NO: 27)
Fwd 5'-ATCCAAGTGTCCTCTGATGGT-3', (SEQ ID NO: 28)
Rev 5'-GCCAAGTGCCTTCCAGTAAGA-3';

ZBTB20 (amplicon size 77 bp)
                                  (SEQ ID NO: 29)
Fwd 5'-GACAGGATCTACTCGGCACTC-3', (SEQ ID NO: 30)
Rev 5'-ACTGCGCCGCTGTAAAAAGA-3';
and ZEB1 (amplicon size 86 bp)
                                  (SEQ ID NO: 31)
Fwd 5'-GATGATGAATGCGAGTCAGATGC-3', (SEQ ID NO: 32)
Rev 5'-ACAGCAGTGTCTTGTTGTTGT-3'.
```

Immunoblotting. For the positive and negative controls, UCLA1 hESCs harboring a homozygous TFAP2C deletion or a doxycycline-inducible TFAP2C expression cassette are used as previously described Pastor et al. (2018). In all cases, hPSCs are first washed with cold PBS and then collected for protein in RIPA lysis buffer with protease inhibitors (ThermoFisher, 78425) and phosphatase inhibitors (ThermoFisher, 78420). RIPA buffer is added to the cells followed by 5 minutes incubation on ice. Cells are then scraped off from the culture dishes, transferred to a microcentrifuge tube, and rotated for 10 minutes at 4° C. If a lysate is too viscous, it is sonicated. Lysates are centrifuged at maximum speed for 15 minutes at 4° C. and the supernatant collected and snap frozen in liquid nitrogen followed by storage at −80° C. Protein lysates are then mixed with loading dye containing β-mercaptoethanol and placed in a 95° C. shaking heating block followed by centrifugation at maximum speed for 2 minutes. The heated lysates are run on SurePage gels (GenScript, M00652) in MOP buffer (GenScript, M00138) for 45 minutes to 1 hour at 120 V, and the proteins then transferred onto 0.45 μm nitrocellulose membranes in Tris Glycine buffer for 2 hours on ice at 300 mA. Protein transfer membranes are blocked in 5% skim milk (Bio-Rad, 170-6404) for 1 hour and incubated with primary antibodies (rabbit anti TFAP2C/AP2 Abcam GR59885-7 at 1:1000 and goat anti GAPDH Abcam ab94583 at 1:1000) on a shaker at 4° C. overnight. After three 5-minute washes, membranes are incubated with secondary antibodies conjugated with HRP in 5% skim milk on the shaker for 2 hours at room temperature. SuperSignal West Femto Maximum Sensitivity Substrate (ThermoFisher, 34095) or Pierce ECL 2 Western Blotting Substrate (ThermoFisher, 80197) are used for chemiluminescent detection. Membranes are scanned using a Sapphire RGBNIRTM Biomolecular Imager (Azure Biosystems, Inc.), and acquired digital images quantified using the ImageJ gel function. TFAP2C protein levels are normalized to GAPDH and reported as mean±SEM for at least four biological replicates.

Mass spectrometry. To understand which protein factor(s) in the MEF-conditioned medium might impact the ability of hPSCs to effectively form cortical organoids, a mass spectrometry-based protein identification experiment was conducted as follows: Conditioned media was collected after 24 hours incubation with or without MEFs. The protein fractions of the samples are enriched by using an Amicon Ultra-15 Centrifugal Filter Unit with Ultracel-10 membrane (Millipore, UFC901024). Concentrated protein samples are then separated by SDS-PAGE and the gel is processed for Coomassie Brilliant Blue staining (Thermo Scientific) according to the manufacturer's instructions. Coomassie Blue-stained bands are cut from the gels, washed twice with 50% acetonitrile, and processed for liquid chromatography tandem mass spectrometry.

Multilayered organ-on-a-chip fabrication. The multilayered organ-on-a-chip system of the disclosure is fabricated using stereolithographic 3D-printing techniques and solution cast-molding processes. The mold for the microfluidic channels is produced using 3D printers. For the multilayered organ-on-a-chip system, two molds are fabricated, the upper block and the lower block. Prior to use, the surfaces of the molds are coated with trichloro(1H,1H,2H,2H-perfluorooctyl) silane (Sigma-Aldrich, St. Louis, MO, USA). Sylgard 184 PDMS two-part elastomer (ratio of 10:1 pre-polymer to curing agent; Dow Corning Corporation, Midland, MI, USA) is mixed, poured into the molds to produce a 4-mm-thick PDMS upper layer and a 0.5-mm-thick PDMS lower layer, and degassed by using a vacuum desiccator for 1 h. The PDMS of the lower block is fixed on a glass slide. The PDMS material is then cured in an oven at 65° C. for 24 h. After curing, the PDMS form is removed from the molds, trimmed, and cleaned. A clear polyester (PET) membrane (pore size of 0.4 μm, thickness of 10 μm, and nominal pore density of $4 \times 10^6$ pores $cm^{-2}$) is fixed on each chamber of the lower and upper PDMS blocks.

Seeding the Multilayered organ-on-a-chip system with Organoids. Each of the four chambers are loaded with an organoid embedded in a PNIPAAm-PEG 3D thermoreversible hydrogel. The blocks are then joined together with clamps. After which, a gradient of different factors can be introduced into the top and bottom media chambers.

Organoid characterization and basis for studying neurodevelopment and disease. Using single-cell RNA sequencing, it was found that fragile X mental retardation 1 (FMR1) is highly expressed at early stages in the human fetal cortex, including progenitors, excitatory, and inhibitory neurons (see FIG. 2A-E). Thus, FMR1 likely plays an important role in neurodevelopment and neural network activities. The organoid system provides an important window for studying the function of this important gene. Strikingly, electrophysiological measurements recorded in the organoids are similar to those previously obtained from slices of human fetal cortex from mid-gestational stages. Taken together, our organoid system provides the basis for studying human neurodevelopment and disease.

Investigation into the role of BMP and SHH signaling pathways in interneuronal migration and diversification. The ability to generate topographic organoids containing diverse cell types is essential for accurately understanding disease pathology because different cell types and brain regions are differentially affected in various diseases. Specific brain regions, such as the cortex, hippocampus, and ganglionic eminence, are markedly affected in FXS. In addition, different types of excitatory and inhibitory neurons are known to play differential and important roles in FXS. Thus, the ability to generate topographic organoids containing different regions and diverse cell types is important for accurately understanding disease pathology. During development, spatially distinct organizers secrete patterning molecules to form signaling gradients that, in turn, specify positional and cell identity. For example, high levels of SHH provide ventral patterning to form the lateral and medial ganglionic eminence (GE) and preoptic area (POA) in the telencephalon, whereas high concentrations of BMPs/WNTs provide dorsal patterning to form the dorsomedial telencephalon (DMT) (see FIG. 3A). In addition to the role of cell specification and diversification, morphogens play an important role in cell migration and guidance. To achieve a precise topographic organization, a device for a multilayered organoid-on-a-ship system was designed that provides consistent concentration gradients of signaling molecules (see FIG. 3B-D), thereby generating forebrain organoids that form the topographic telencephalon.

Achieving precise topographic organization of organoids. The ability to generate topographic organoids containing diverse cell types is important for accurately understanding disease pathology because different cell types and brain regions are differentially affected in various diseases. To achieve precise topographic organization, provided herein is the development of a "multilayered organ-on-a-chip systems" to establish multi-concentration gradients in a 3D environment, mimicking developmental processes to create a properly formed telencephalon including the GE, cortex with defined areal identities, DMT, LGE (which partially gives rise to amygdala), and MGE (see FIG. 3). In the exemplary multilayered organ-on-a-chip system, the top media chamber contains high concentrations of dorsalizing/caudalizing factors (BMP4 and WNT3A) and the bottom media chamber contains high concentrations of a ventralizing or rostralizing factor (SHH or FGF8) (see FIG. 3B). Natural diffusion through the porous membranes establishes opposing BMP4/WNT3A and SHH/FGF8 gradients (see FIG. 2B). The organoid is embedded in a hydrogel (PNI-PAAm-PEG 3D thermoreversible) and the concentration of the hydrogel controls the steepness of the morphogen gradients, which will be sustained for six days—the period required to specify dorsal and ventral identities. In addition, this design avoids media flow in the organoid chamber that would cause shear stress and could disrupt normal cellular function. It is expected that the continuous and consistent formation of the entire telencephalon provides unprecedented opportunities for studying basic mechanisms of tissue formation and disease modeling in a diverse and complex tissue setting, as seen in the human forebrain.

Immunochemical analyses will then be used to visualize different cell domains using cell specific markers. Using immunohistochemistry, the number of inhibitory neurons in the cortical area will be evaluated for consistency across different time points and experiments. Quantification of the topographic organoids will be carried out to determine if an 80% excitatory: 20% inhibitory neuron ratio is achieved. Single-cell RNA-sequencing (scRNA-seq) is carried out to measure molecular features and to catalog the cell types. After which, the resulting data is compared against published human fetal scRNA-seq data.

Investigating the role of FMR1 dysfunction in interneuronal migration and differentiation and cortical neural network activities in topographic telencephalic organoids. It was postulated that FMR1 dysfunction affects interneuronal migration leading to changes in BMP-mediated interneuronal differentiation, and FMR1 dysfunction leads to defects in neural network activities. To test the foregoing, topographic telencephalic organoids from FXS-patient derived and healthy hPSC lines are generated. Using these FXS organoids, it can then be determined if FMR1 dysfunction affects molecular signatures in FXS topographic organoids; and whether FMR1 dysfunction leads to species-specific molecular signatures. using scRNA-seq, it will be examined how transcriptomes of topographic organoids derived from FXS hiPSC differ from those derived from typically developing hiPSCs and/or isogenic control FXS hiPSCs across different time points. Changes in the transcriptomes of FXS knockout mice in comparison wild-type transcriptomes at E15.5 (peak of neurogenesis) and PO (end of neurogenesis) are then evaluated. Combining scRNA-seq analyses from organoid and murine models are used to establish signatures that are distinct among species. Accordingly, the topographic organoid system of the disclosure allows for the recapitulation of FXS patient phenotypes and further, can be used as a model or tool to investigate additional human-specific molecular and cellular mechanisms of FXS pathologies.

A number of embodiments have been described herein. Nevertheless, it will be understood that various modifications may be made without departing from the spirit and scope of this disclosure. Accordingly, other embodiments are within the scope of the following claims.

---

What is claimed is:

1. A multilayered organ-on-a-chip system configured to generate three-dimensional molecular gradients, comprising:

an organoid chamber configured to accommodate an organoid;

a first porous membrane located on one side of the organoid chamber, wherein the first porous membrane allows for diffusion of a first fluid and a third fluid comprising cell factor(s), growth factor(s), cytokine(s) and/or differentiation factor(s) through the first porous membrane into the organoid chamber;

a second porous membrane located on the opposite side of the organoid chamber from the first porous membrane, wherein the second porous membrane allows for diffusion of a second fluid and a fourth fluid comprising cell factor(s), growth factor(s), cytokine(s) and/or differentiation factor(s) through the second porous membrane into the organoid chamber;

a first fluid inlet channel that is contact with the organoid chamber on one end and an inlet port on the other end that is connected to a first fluid reservoir containing the first fluid, wherein the first fluid channel is in fluid communication with the organoid chamber via the first porous membrane;

a second fluid inlet channel that is in contact with the organoid chamber on one end and an inlet port on the other end that is connected to a second fluid reservoir containing the second fluid, wherein the second fluid inlet channel is in fluid communication with the organoid chamber via the second porous membrane;

a third fluid inlet channel that is contact with organoid chamber on one end and an inlet port on the other end that is connected to a third fluid reservoir containing the third fluid, wherein the third fluid inlet channel is in fluid communication with the organoid chamber via the first porous membrane;

a fourth fluid inlet channel that is in contact with the organoid chamber on one end and an inlet port on the other end that is connected to a fourth fluid reservoir containing the fourth fluid, wherein the fourth fluid inlet channel is in fluid communication with the organoid chamber via the second porous membrane;
a first fluid outlet channel that is contact with organoid chamber, wherein the first fluid outlet channel is in fluid communication with the organoid chamber via the first porous membrane;
a second fluid outlet channel that is contact with organoid chamber, wherein the second fluid outlet channel is in fluid communication with the organoid chamber via the second porous membrane;
wherein the first fluid inlet channel, the second fluid inlet channel, the third fluid inlet channel, and the fourth fluid inlet channel are configured to flow fluids into the channels in a directional manner from the inlet ports to the organoid chamber;
wherein the first fluid outlet channel is configured to flow fluids from the organoid chamber to a first outlet port in a directional manner;
wherein the second fluid outlet channel flow is configured to flow fluids from the organoid chamber to a second outlet port in a directional manner;
wherein introduction of the first, second, third and fourth fluids into the organoid chamber via the fluid inlet channels generates molecular gradients by natural diffusion of factors found in the fluids into the organoid chamber, and
wherein the molecular gradient that diffuses into the organoid chamber via the first porous membrane is different than the molecular gradient that diffuses into the organoid chamber via the second porous membrane.

2. The multilayered organ-on-a-chip system of claim 1, wherein the first porous membrane and the second porous membrane are comprised of a material selected from polyethylene terephthalate (PET), polycarbonate (PC), macro porous silicon, hydrophilic polytetrafluoroethylene (PTFE), polydimethylsiloxane (PDMS), cyclo olefin polymer (COP), cyclo olefin co-polymer (COC), polystyrene (PS), polyvinyl chloride (PVC) polymethylmethacrylate (PMMA) and/or mixed cellulose esters.

3. The multilayered organ-on-a-chip system of claim 1, wherein the organoid chamber comprises a primitive neuroepithelial organoid embedded in a hydrogel.

4. The multilayered organ-on-a-chip system of claim 3, wherein the primitive neuroepithelial organoid is neurally differentiated from hPSCs, iPSCs, or ESCs.

5. The multilayered organ-on-a-chip system of claim 4, wherein the hPSCs, iPSCs, or ESCs are generated from cells of a subject that has a genetic neurological disorder.

6. The multilayered organ-on-a-chip system of claim 5, wherein the genetic neurological disorder is selected from the group consisting of Aicardi Syndrome, Alper's Disease, Batten Disease, Fabry Disease, Fahr's Syndrome, Gerstmann-Straussler-Scheinker Disease, Leigh's Disease, Lesch-Nyhan Syndrome, Menkes Disease, Moya Moya Disease, Niemann-Pick Disease, Zellweger Syndrome, Fragile X Syndrome, 2-hydroxygluraric aciduria, 3-hydroxy-3-methylglutaryl-CoA lyase deficiency, 3-methylcrotonyl-CoA carboxylase deficiency, adenylosuccinate lyase deficiency, alpha-mannosidosis, alpha-methylacyl-CoA racemase deficiency, aminoacylase 1 deficiency, arginase deficiency, argininosuccinic aciduria, aromatic L-amino acid decarboxylase deficiency, aspartylglucosaminuria, beta-ketothiolase deficiency, beta-mannosidosis, biotinidase deficiency, childhood myocerebrohepatopathy spectrum, citrullinemia, Coats plus syndrome, combined malonic and methylmalonic aciduria, dentatorubral-pallidoluysian atrophy, deoxyguanosine kinase deficiency, dihydrolipoamide dehydrogenase deficiency, dihydropyrimidine dehydrogenase deficiency, ethylmalonic encephalopathy, fucosidosis, fumarase deficiency, GABA-transaminase deficiency, galactosemia, GLUT1 deficiency syndrome, glutamate formiminotransferase deficiency, glutaric acidemia type I, glutathione synthetase deficiency, GM1 gangliosidosis, GRIN2B-related neurodevelopmental disorder, guanidinoacetate methyltransferase deficiency, hypermethioninemia, hyperprolinemia, isovaleric acidemia, L1 syndrome, Leigh syndrome, malonyl-CoA decarboxylase deficiency, MECP2-related severe neonatal encephalopathy, MEGDEL syndrome, mitochondrial complex III deficiency, mitochondrial neurogastrointestinal encephalopathy disease, molybdenum cofactor deficiency, mucolipidosis type IV, mucopolysaccharidosis type I, mucopolysaccharidosis type II, mucopolysaccharidosis type III, multiple sulfatase deficiency, myoclonic epilepsy with ragged-red fibers, N-acetylglutamate synthase deficiency, nonketotic hyperglycinemia, ornithine transcarbamylase deficiency, phosphoglycerate dehydrogenase deficiency, phosphoglycerate kinase deficiency, phosphoribosylpyrophosphate synthetase superactivity, PMM2-congenital disorder of glycosylation, prion disease, prolidase deficiency, pyruvate dehydrogenase deficiency, Schindler disease, short/branched chain acyl-CoA dehydrogenase deficiency, sialic acid storage disease, succinic semialdehyde dehydrogenase deficiency, and X-linked creatine deficiency.

7. The multilayered organ-on-a-chip system of claim 6, wherein the genetic neural disorder is Fragile X Syndrome.

8. The multilayered organ-on-a-chip system of claim 3, wherein the introduction of the fluids generates a multi-concentration gradient that promotes the further differentiation of the primitive neuroepithelial organoid into a topographic neural organoid.

9. The multilayered organ-on-a-chip system of claim 8, wherein the topographic neural organoid is a brain organoid, a cortical organoid, or a ganglionic eminence organoid.

10. The multilayered organ-on-a-chip system of claim 9, wherein the brain organoid has topographic organization of the choroid plexus, hippocampal, cortical, antihem, and/or lateral and media ganglionic eminence regions.

11. The multilayered organ-on-a-chip system of claim 9, wherein the brain organoid is a brain organoid derived from cells of a subject that has a genetic neurological disorder.

12. The multilayered organ-on-a-chip system of claim 11, wherein the brain organoid is a Fragile X Syndrome brain organoid.

13. The multilayered organ-on-a-chip system of claim 1, wherein the first fluid comprises different types and/or different concentrations of cell factor(s), growth factor(s), cytokine(s) and/or differentiation factor(s) than the second fluid.

14. The multilayered organ-on-a-chip system of claim 1, wherein the first fluid comprises high concentrations of dorsalizing/caudalizing factors.

15. The multilayered organ-on-a-chip system of claim 14, wherein the dorsalizing/caudalizing factors is BMP4 and WNT3A.

16. The multilayered organ-on-a-chip system of claim 1, wherein the second fluid comprises high concentrations of a ventralizing or rostralizing factor.

17. The multilayered organ-on-a-chip system of claim 16, wherein the ventralizing or rostralizing factor is SHH or FGF8.

18. The multilayered organ-on-a-chip system of claim 1, wherein the multilayered organ-on-a-chip system further comprises:
   an organoid inlet port that is connected to the organoid chamber which is configured for introducing a solution comprising a thermoresponsive hydrogel and an organoid into the organoid chamber.

\* \* \* \* \*